Figure 1:
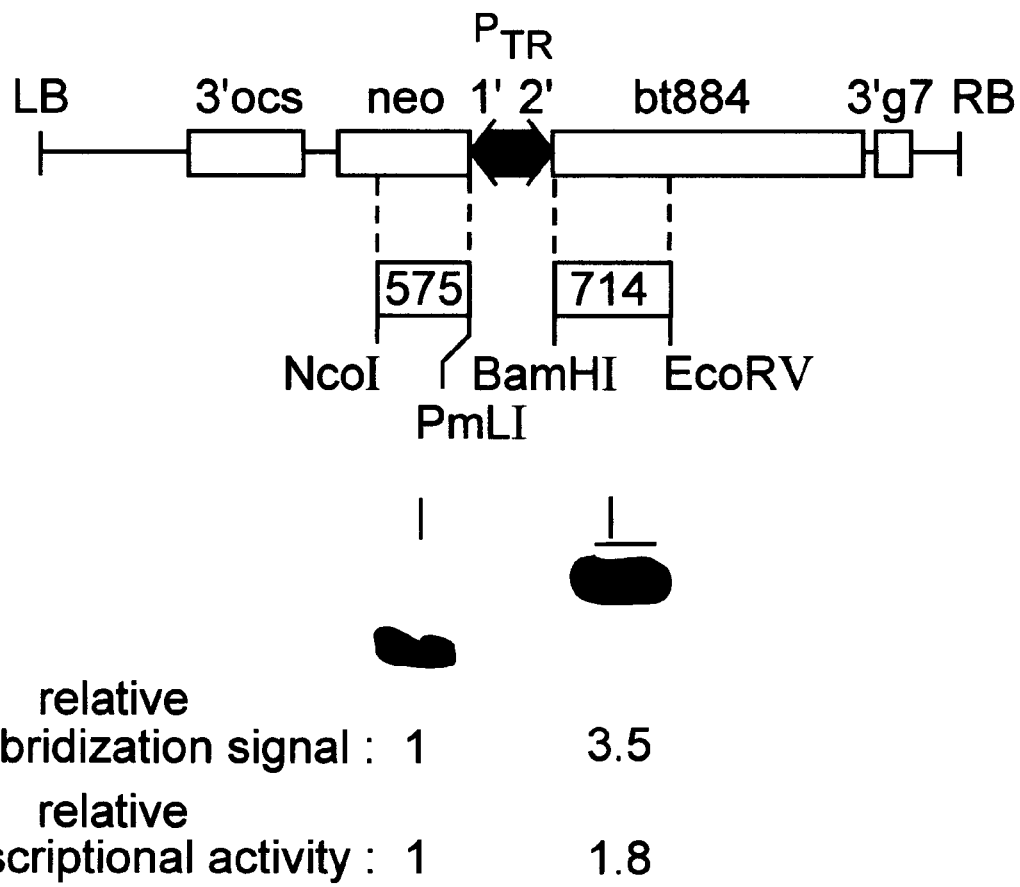

United States Patent [19]

Cornelissen et al.

[11] Patent Number: 5,952,547
[45] Date of Patent: Sep. 14, 1999

[54] MODIFIED *BACILLUS THURINGIENSIS* GENES WITH IMPROVED EXPRESSION IN PLANT CELLS, METHODS OF PRODUCTION ON AND USE

[75] Inventors: Marc Cornelissen, Heusden; Piet Soetaert, Laarne, both of Belgium; Maike Stam, Al Amstelveen, Netherlands; Jan Dockx, Turnhout; Roel Van Aarssen, Gent, both of Belgium

[73] Assignee: Plant Genetic Systems, N.V., Brussels, Belgium

[21] Appl. No.: 08/232,016

[22] PCT Filed: Oct. 30, 1992

[86] PCT No.: PCT/EP92/02547

§ 371 Date: Nov. 3, 1994

§ 102(e) Date: Nov. 3, 1994

[87] PCT Pub. No.: WO93/09218

PCT Pub. Date: May 13, 1993

[30] Foreign Application Priority Data

Oct. 30, 1991 [EP] European Pat. Off. ............... 91402920
Mar. 25, 1992 [EP] European Pat. Off. ............... 92400820

[51] Int. Cl.$^6$ .............................. A01H 5/00; C12N 5/14; C12N 15/32; C12N 15/82
[52] U.S. Cl. .................. 800/302; 204/456; 435/91.2; 435/320.1; 435/419; 435/468; 536/23.71; 800/279
[58] Field of Search .................. 536/23.71; 800/205, 800/250; 435/240.4, 172.3, 320.1, 172.1, 419, 91.2; 204/456

[56] References Cited

U.S. PATENT DOCUMENTS 5,380,831 1/1995 Adang et al. ................... 536/23.71
5,550,365 8/1996 Fischhoff et al. ................... 435/240.4

FOREIGN PATENT DOCUMENTS 0 359 472   3/1990  European Pat. Off. .
0359472     3/1990  European Pat. Off. ........ C12N 15/82
90/10076    9/1990  WIPO .
91/16432    10/1991 WIPO .

OTHER PUBLICATIONS

Vaeck et al. (1987) Nature vol. 328: pp. 33–37 Jul. 1987.

*Proceedings of the National Academy of Sciences of USA*, "Modification of the Coding Sequence Enhances Plant Expression of Insect Control Protein Genes", Perlack, et al., vol. 88, Apr. 1991, pp. 3324–3328.

*Plant Molecular Biology*, "Analysis of Unstable RNA Transcipts on Insecticidal Crystal Protein Genes of *Bacillus thuringiensis* in Transgenic Plants and Electroportated Protoplasts", Murray et al., vol. 16, Jun. 1991, pp. 1035–1050.

*Nature*, "Transgenic Plants Protected from Insect Attack", Vaeck, et al., vol. 328, Jul. 1987, pp. 33–37.

*Primary Examiner*—Douglas W. Robinson
*Assistant Examiner*—Amy J. Nelson
*Attorney, Agent, or Firm*—Burns, Doane, Swecker & Mathis, LLP

[57] ABSTRACT

The invention relates to modified *Bacillus thurigiensis* genes with improved expression in plant cells, their preparation and uses. The invention relates more particularly to DNA fragments encoding all or part of a Bt insecticidal crystal protein, modified by translationally neutral modification(s) in cryptic promoter(s) and/or abortive intron(s). The invention also discloses method of preparing such modified DNAs, and methods of protecting plants from an insect pest.

27 Claims, 4 Drawing Sheets

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
        (A) ORGANISM: oligonucleotide, designated as PS48

(xi) SEQUENCE DESCRIPTION: SEQ ID NO:1:

CATGCTGTAC GCTGGTACAA TACGGG                                              26

(2) INFORMATION FOR SEQ ID NO:2:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: oligonucleotide, designated as PS43

(xi) SEQUENCE DESCRIPTION: SEQ ID NO:2:

GGACTCCTAA TACTTCCTTC TATGCCCTG                                           29

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: oligonucleotide, designated as PS38

(xi) SEQUENCE DESCRIPTION: SEQ ID NO:3:

GGCGACATGG CCGCTGAGAA TCTG                                                24

(2) INFORMATION FOR SEQ ID NO:4:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: oligonucleotide, designated as PS39

(xi) SEQUENCE DESCRIPTION: SEQ ID NO:4:

CAGATTCTCA G                                                              11

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: oligonucleotide, designated as PS47

(xi) SEQUENCE DESCRIPTION: SEQ ID NO:5:

GCTGGTACAA TACGGGATTA GAGCG                                               25

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: oligonucleotide, designated as PS44

(xi) SEQUENCE DESCRIPTION: SEQ ID NO:6:

```
CCTTCTATGC CCTGAGCCGA GCCTCG                                      26
```

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: oligonucleotide, designated as PS38

(xi) SEQUENCE DESCRIPTION: SEQ ID NO:7:

```
GGCGACATGG CCGCTGAGAA TCTG                                        24
```

(2) INFORMATION FOR SEQ ID NO:8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: oligonucleotide, designated as PS46

(xi) SEQUENCE DESCRIPTION: SEQ ID NO:8:

```
TACGGGATTA GAGCGTGTAT GGGGAC                                      26
```

(2) INFORMATION FOR SEQ ID NO:9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: oligonucleotide, designated as PS45

(xi) SEQUENCE DESCRIPTION: SEQ ID NO:9:

```
GCCGAGCCTC GAAAACTACC ATC                                         23
```

(2) INFORMATION FOR SEQ ID NO:10:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
     (A) ORGANISM: oligonucleotide, designated as PS58

(xi) SEQUENCE DESCRIPTION: SEQ ID NO:10:

GTGCCACCTA GGCAAGGATT TAGTCATCG                                         29

(2) INFORMATION FOR SEQ ID NO:11:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: oligonucleotide, designated as PS59

(xi) SEQUENCE DESCRIPTION: SEQ ID NO:11:

TAGCTCATCG GGGGATCTGC TAGAGCCGG                                          29

(2) INFORMATION FOR SEQ ID NO:12:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: oligonucleotide, designated as PS61

(xi) SEQUENCE DESCRIPTION: SEQ ID NO:12:

ACATTGCCGT AGATGAAAGA CTGAGTGCG                                          29

(2) INFORMATION FOR SEQ ID NO:13:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: oligonucleotide, designated as PS62

(xi) SEQUENCE DESCRIPTION: SEQ ID NO:13:

CCCCAATCGA TATTTCCTTG TCGCTAACG                                          29

(2) INFORMATION FOR SEQ ID NO:14:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: oligonucleotide, designated as PS63

(xi) SEQUENCE DESCRIPTION: SEQ ID NO:14:

```
TTGGACAAAG GTGGGGATTT GATGCCGCG                                                29

(2) INFORMATION FOR SEQ ID NO:15:

(i) SEQUENCE CHARACTERISTICS:
           (A) LENGTH: 29 base pairs
           (B) TYPE: nucleic acid
           (C) STRANDEDNESS: single
           (D) TOPOLOGY: linear (ii) MOLECULE TYPE: DNA (genomic)

(vi) ORIGINAL SOURCE:
           (A) ORGANISM: oligonucleotide, designated as PS64

(xi) SEQUENCE DESCRIPTION: SEQ ID NO:15:

ATCCGGTCCC CATACACGCT CTAATCCCG                                                29

(2) INFORMATION FOR SEQ ID NO:16:

(i) SEQUENCE CHARACTERISTICS:
           (A) LENGTH: 29 base pairs
           (B) TYPE: nucleic acid
           (C) STRANDEDNESS: single
           (D) TOPOLOGY: linear (ii) MOLECULE TYPE: DNA (genomic)

(vi) ORIGINAL SOURCE:
           (A) ORGANISM: oligonucleotide, designated as PS65

(xi) SEQUENCE DESCRIPTION: SEQ ID NO:16:

ATGGCTTAAT CGATGACTAA ATCCTTGCC                                                29

(2) INFORMATION FOR SEQ ID NO:17:

(i) SEQUENCE CHARACTERISTICS:
           (A) LENGTH: 29 base pairs
           (B) TYPE: nucleic acid
           (C) STRANDEDNESS: single
           (D) TOPOLOGY: linear (ii) MOLECULE TYPE: DNA (genomic)

(vi) ORIGINAL SOURCE:
           (A) ORGANISM: oligonucleotide, designated as PS66

(xi) SEQUENCE DESCRIPTION: SEQ ID NO:17:

CCAAATCGAT GGATCCCGAT AACAATCCG                                                29

(2) INFORMATION FOR SEQ ID NO:18:

(i) SEQUENCE CHARACTERISTICS:
           (A) LENGTH: 37 base pairs
           (B) TYPE: nucleic acid
           (C) STRANDEDNESS: single
           (D) TOPOLOGY: linear (ii) MOLECULE TYPE: DNA (genomic)

(vi) ORIGINAL SOURCE:
           (A) ORGANISM: oligonucleotide, designated as RVA-5a (xi) SEQUENCE DESCRIPTION: SEQ ID NO:18:

ACGTATCCGA TTCGAACAGT TTCCCAGTTA ACAAGAG                                       37

(2) INFORMATION FOR SEQ ID NO:19:

(i) SEQUENCE CHARACTERISTICS:
           (A) LENGTH: 37 base pairs
           (B) TYPE: nucleic acid
```

(C) STRANDEDNESS: single
          (D) TOPOLOGY: linear (ii) MOLECULE TYPE: DNA (genomic)

(vi) ORIGINAL SOURCE:
          (A) ORGANISM: oligonucleotide, designated as RVA-5b (xi) SEQUENCE DESCRIPTION: SEQ ID NO:19:

ACGTATCCGA TTCGAACAGT TTCCCAGCTA ACAAGAG                                37

(2) INFORMATION FOR SEQ ID NO:20:

(i) SEQUENCE CHARACTERISTICS:
          (A) LENGTH: 37 base pairs
          (B) TYPE: nucleic acid
          (C) STRANDEDNESS: single
          (D) TOPOLOGY: linear (ii) MOLECULE TYPE: DNA (genomic)

(vi) ORIGINAL SOURCE:
          (A) ORGANISM: oligonucleotide, designated as RVA-6a (xi) SEQUENCE DESCRIPTION: SEQ ID NO:20:

CTCTTGTTAA CTGGGAAACT GTTCGAATCG GATACGT                                37

(2) INFORMATION FOR SEQ ID NO:21:

(i) SEQUENCE CHARACTERISTICS:
          (A) LENGTH: 37 base pairs
          (B) TYPE: nucleic acid
          (C) STRANDEDNESS: single
          (D) TOPOLOGY: linear (ii) MOLECULE TYPE: DNA (genomic)

(vi) ORIGINAL SOURCE:
          (A) ORGANISM: oligonucleotide, designated as RVA-6b (xi) SEQUENCE DESCRIPTION: SEQ ID NO:21:

CTCTTGTTAG CTGGGAAACT GTTCGAATCG GATACGT                                37

(2) INFORMATION FOR SEQ ID NO:22:

(i) SEQUENCE CHARACTERISTICS:
          (A) LENGTH: 7639 base pairs
          (B) TYPE: nucleic acid
          (C) STRANDEDNESS: double
          (D) TOPOLOGY: circular (ii) MOLECULE TYPE: DNA (genomic)

(vi) ORIGINAL SOURCE:
          (A) ORGANISM: plasmid DNA designated as pJD884

(ix) FEATURE:
          (A) NAME/KEY: CDS
          (B) LOCATION: 1..1869
          (D) OTHER INFORMATION: /note= "Coding region of a
              truncated bt2 (cryIAb) gene, also designated as the bt884
              gene."

(ix) FEATURE:
          (A) NAME/KEY: misc_feature
          (B) LOCATION: 1877..2110
          (D) OTHER INFORMATION: /note= "3' regulatory sequence
              containing the polyadenylation site derived from
              Agrobacterium T-DNA gene 7."

(ix) FEATURE:
          (A) NAME/KEY: misc_feature
          (B) LOCATION: 2480..3005
          (D) OTHER INFORMATION: /note= "35S promoter sequence -continued (ix) FEATURE:
    (A) NAME/KEY: misc_feature
    (B) LOCATION: 3006..3665
    (D) OTHER INFORMATION: /note= "Coding sequence of
        chloramphenicol acetyl transferase gene."

(ix) FEATURE:
    (A) NAME/KEY: misc_feature
    (B) LOCATION: 3666..4491
    (D) OTHER INFORMATION: /note= "3' regulatory sequence
        containing the polyadenylation site derived from
        Agrobacterium T-DNA octopine synthase gene."

(ix) FEATURE:
    (A) NAME/KEY: misc_feature
    (B) LOCATION: 5684..6541
    (D) OTHER INFORMATION: /note= "Sequence complementary to
        the coding sequence of the beta-lactamase gene."

(ix) FEATURE:
    (A) NAME/KEY: misc_feature
    (B) LOCATION: 7155..7639
    (D) OTHER INFORMATION: /note= "TR1' and TR2' promoter
        derived from Agrobacterium T-DNA."

(xi) SEQUENCE DESCRIPTION: SEQ ID NO:22:

```
ATG GAT CCC GAT AAC AAT CCG AAC ATC AAT GAA TGC ATT CCT TAT AAT       48
Met Asp Pro Asp Asn Asn Pro Asn Ile Asn Glu Cys Ile Pro Tyr Asn
 1               5                  10                  15

TGT TTA AGT AAC CCT GAA GTA GAA GTA TTA GGT GGA GAA AGA ATA GAA       96
Cys Leu Ser Asn Pro Glu Val Glu Val Leu Gly Gly Glu Arg Ile Glu
            20                  25                  30

ACT GGT TAC ACC CCA ATC GAT ATT TCC TTG TCG CTA ACG CAA TTT CTT      144
Thr Gly Tyr Thr Pro Ile Asp Ile Ser Leu Ser Leu Thr Gln Phe Leu
        35                  40                  45

TTG AGT GAA TTT GTT CCC GGT GCT GGA TTT GTG TTA GGA CTA GTT GAT      192
Leu Ser Glu Phe Val Pro Gly Ala Gly Phe Val Leu Gly Leu Val Asp
 50                  55                  60

ATA ATA TGG GGA ATT TTT GGT CCC TCT CAA TGG GAC GCA TTT CTT GTA      240
Ile Ile Trp Gly Ile Phe Gly Pro Ser Gln Trp Asp Ala Phe Leu Val
 65                  70                  75                  80

CAA ATT GAA CAG TTA ATT AAC CAA AGA ATA GAA GAA TTC GCT AGG AAC      288
Gln Ile Glu Gln Leu Ile Asn Gln Arg Ile Glu Glu Phe Ala Arg Asn
                85                  90                  95

CAA GCC ATT TCT AGA TTA GAA GGA CTA AGC AAT CTT TAT CAA ATT TAC      336
Gln Ala Ile Ser Arg Leu Glu Gly Leu Ser Asn Leu Tyr Gln Ile Tyr
            100                 105                 110

GCA GAA TCT TTT AGA GAG TGG GAA GCA GAT CCT ACT AAT CCA GCA TTA      384
Ala Glu Ser Phe Arg Glu Trp Glu Ala Asp Pro Thr Asn Pro Ala Leu
        115                 120                 125

AGA GAA GAG ATG CGT ATT CAA TTC AAT GAC ATG AAC AGT GCC CTT ACA      432
Arg Glu Glu Met Arg Ile Gln Phe Asn Asp Met Asn Ser Ala Leu Thr
130                 135                 140

ACC GCT ATT CCT CTT TTT GCA GTT CAA AAT TAT CAA GTT CCT CTT TTA      480
Thr Ala Ile Pro Leu Phe Ala Val Gln Asn Tyr Gln Val Pro Leu Leu
145                 150                 155                 160

TCA GTA TAT GTT CAA GCT GCA AAT TTA CAT TTA TCA GTT TTG AGA GAT      528
Ser Val Tyr Val Gln Ala Ala Asn Leu His Leu Ser Val Leu Arg Asp
                165                 170                 175

GTT TCA GTG TTT GGA CAA AGG TGG GGA TTT GAT GCC GCG ACT ATC AAT      576
Val Ser Val Phe Gly Gln Arg Trp Gly Phe Asp Ala Ala Thr Ile Asn
            180                 185                 190

AGT CGT TAT AAT GAT TTA ACT AGG CTT ATT GGC AAC TAT ACA GAT CAT      624
Ser Arg Tyr Asn Asp Leu Thr Arg Leu Ile Gly Asn Tyr Thr Asp His
        195                 200                 205
```

```
GCT GTA CGC TGG TAC AAT ACG GGA TTA GAG CGT GTA TGG GGA CCG GAT       672
Ala Val Arg Trp Tyr Asn Thr Gly Leu Glu Arg Val Trp Gly Pro Asp
    210                 215                 220

TCT AGA GAT TGG ATA AGA TAT AAT CAA TTT AGA AGA GAA TTA ACA CTA       720
Ser Arg Asp Trp Ile Arg Tyr Asn Gln Phe Arg Arg Glu Leu Thr Leu
225                 230                 235                 240

ACT GTA TTA GAT ATC GTT TCT CTA TTT CCG AAC TAT GAT AGT AGA ACG       768
Thr Val Leu Asp Ile Val Ser Leu Phe Pro Asn Tyr Asp Ser Arg Thr
                245                 250                 255

TAT CCA ATT CGA ACA GTT TCC CAA TTA ACA AGA GAA ATT TAT ACA AAC       816
Tyr Pro Ile Arg Thr Val Ser Gln Leu Thr Arg Glu Ile Tyr Thr Asn
                    260                 265                 270

CCA GTA TTA GAA AAT TTT GAT GGT AGT TTT CGA GGC TCG GCT CAG GGC       864
Pro Val Leu Glu Asn Phe Asp Gly Ser Phe Arg Gly Ser Ala Gln Gly
                275                 280                 285

ATA GAA GGA AGT ATT AGG AGT CCA CAT TTG ATG GAT ATA CTT AAC AGT       912
Ile Glu Gly Ser Ile Arg Ser Pro His Leu Met Asp Ile Leu Asn Ser
290                 295                 300

ATA ACC ATC TAT ACG GAT GCT CAT AGA GGA GAA TAT TAT TGG TCA GGG       960
Ile Thr Ile Tyr Thr Asp Ala His Arg Gly Glu Tyr Tyr Trp Ser Gly
305                 310                 315                 320

CAT CAA ATA ATG GCT TCT CCT GTA GGG TTT TCG GGG CCA GAA TTC ACT      1008
His Gln Ile Met Ala Ser Pro Val Gly Phe Ser Gly Pro Glu Phe Thr
                325                 330                 335

TTT CCG CTA TAT GGA ACT ATG GGA AAT GCA GCT CCA CAA CAA CGT ATT      1056
Phe Pro Leu Tyr Gly Thr Met Gly Asn Ala Ala Pro Gln Gln Arg Ile
                340                 345                 350

GTT GCT CAA CTA GGT CAG GGC GTG TAT AGA ACA TTA TCG TCC ACT TTA      1104
Val Ala Gln Leu Gly Gln Gly Val Tyr Arg Thr Leu Ser Ser Thr Leu
                355                 360                 365

TAT AGA AGA CCT TTT AAT ATA GGG ATA AAT AAT CAA CAA CTA TCT GTT      1152
Tyr Arg Arg Pro Phe Asn Ile Gly Ile Asn Asn Gln Gln Leu Ser Val
370                 375                 380

CTT GAC GGG ACA GAA TTT GCT TAT GGA ACC TCC TCA AAT TTG CCA TCC      1200
Leu Asp Gly Thr Glu Phe Ala Tyr Gly Thr Ser Ser Asn Leu Pro Ser
385                 390                 395                 400

GCT GTA TAC AGA AAA AGC GGA ACG GTA GAT TCG CTG GAT GAA ATA CCG      1248
Ala Val Tyr Arg Lys Ser Gly Thr Val Asp Ser Leu Asp Glu Ile Pro
                405                 410                 415

CCA CAG AAT AAC AAC GTG CCA CCT AGG CAA GGA TTT AGT CAT CGA TTA      1296
Pro Gln Asn Asn Asn Val Pro Pro Arg Gln Gly Phe Ser His Arg Leu
                420                 425                 430

AGC CAT GTT TCA ATG TTT CGT TCA GGC TTT AGT AAT AGT AGT GTA AGT      1344
Ser His Val Ser Met Phe Arg Ser Gly Phe Ser Asn Ser Ser Val Ser
                435                 440                 445

ATA ATA AGA GCT CCT ATG TTC TCT TGG ATA CAT CGT AGT GCT GAA TTT      1392
Ile Ile Arg Ala Pro Met Phe Ser Trp Ile His Arg Ser Ala Glu Phe
450                 455                 460

AAT AAT ATA ATT CCT TCA TCA CAA ATT ACA CAA ATA CCT TTA ACA AAA      1440
Asn Asn Ile Ile Pro Ser Ser Gln Ile Thr Gln Ile Pro Leu Thr Lys
465                 470                 475                 480

TCT ACT AAT CTT GGC TCT GGA ACT TCT GTC GTT AAA GGA CCA GGA TTT      1488
Ser Thr Asn Leu Gly Ser Gly Thr Ser Val Val Lys Gly Pro Gly Phe
                485                 490                 495

ACA GGA GGA GAT ATT CTT CGA AGA ACT TCA CCT GGC CAG ATT TCA ACC      1536
Thr Gly Gly Asp Ile Leu Arg Arg Thr Ser Pro Gly Gln Ile Ser Thr
                500                 505                 510

TTA AGA GTA AAT ATT ACT GCA CCA TTA TCA CAA AGA TAT CGG GTA AGA      1584
Leu Arg Val Asn Ile Thr Ala Pro Leu Ser Gln Arg Tyr Arg Val Arg
                515                 520                 525
```

```
ATT CGC TAC GCT TCT ACC ACA AAT TTA CAA TTC CAT ACA TCA ATT GAC         1632
Ile Arg Tyr Ala Ser Thr Thr Asn Leu Gln Phe His Thr Ser Ile Asp
        530                 535                 540

GGA AGA CCT ATT AAT CAG GGG AAT TTT TCA GCA ACT ATG AGT AGT GGG         1680
Gly Arg Pro Ile Asn Gln Gly Asn Phe Ser Ala Thr Met Ser Ser Gly
545                 550                 555                 560

AGT AAT TTA CAG TCC GGA AGC TTT AGG ACT GTA GGT TTT ACT ACT CCG         1728
Ser Asn Leu Gln Ser Gly Ser Phe Arg Thr Val Gly Phe Thr Thr Pro
                565                 570                 575

TTT AAC TTT TCA AAT GGA TCA AGT GTA TTT ACG TTA AGT GCT CAT GTC         1776
Phe Asn Phe Ser Asn Gly Ser Ser Val Phe Thr Leu Ser Ala His Val
            580                 585                 590

TTC AAT TCA GGC AAT GAA GTT TAT ATA GAT CGA ATT GAA TTT GTT CCG         1824
Phe Asn Ser Gly Asn Glu Val Tyr Ile Asp Arg Ile Glu Phe Val Pro
        595                 600                 605

GCA GAA GTA ACC TTC GAC CTG CAG CCA AGC TTG CTG ATT GAT TGA             1869
Ala Glu Val Thr Phe Asp Leu Gln Pro Ser Leu Leu Ile Asp *
610                 615                 620

CCGGATCGAT CCGGCTCTAG CAGATCCCCC GATGAGCTAA GCTAGCTATA TCATCAATTT       1929
ATGTATTACA CATAATATCG CACTCAGTCT TTCATCTACG GCAATGTACC AGCTGATATA       1989
ATCAGTTATT GAAATATTTC TGAATTTAAA CTTGCATCAA TAAATTTATG TTTTTGCTTG       2049
GACTATAATA CCTGACTTGT TATTTTATCA ATAAATATTT AAACTATATT TCTTTCAAGA       2109
TGGGAATTAA CATCTACAAA TTGCCTTTTC TTATCGACCA TGTACGGGTA CCGAGCTCGA       2169
ATTCCTACGC AGCAGGTCTC ATCAAGACGA TCTACCCGAG TAACAATCTC CAGGAGATCA       2229
AATACCTTCC CAAGAAGGTT AAAGATGCAG TCAAAAGATT CAGGACTAAT TGCATCAAGA       2289
ACACAGAGAA AGACATATTT CTCAAGATCA GAAGTACTAT TCCAGTATGG ACGATTCAAG       2349
GCTTGCTTCA TAAACCAAGG CAAGTAATAG AGATTGGAGT CTCTAAAAAG GTAGTTCCTA       2409
CTGAATCTAA GGCCATGCAT GGAGTCTAAG ATTCAAATCG AGGATCTAAC AGAACTCGCC       2469
GTGAAGACTG GCGAACAGTT CATACAGAGT CTTTTACGAC TCAATGACAA GAAGAAAATC       2529
TTCGTCAACA TGGTGGAGCA CGACACTCTG GTCTACTCCA AAAATGTCAA AGATACAGTC       2589
TCAGAAGACC AAAGGGCTAT TGAGACTTTT CAACAAAGGA TAATTTCGGG AAACCTCCTC       2649
GGATTCCATT GCCCAGCTAT CTGTCACTTC ATCGAAAGGA CAGTAGAAAA GGAAGGTGGC       2709
TCCTACAAAT GCCATCATTG CGATAAAGGA AAGGCTATCA TTCAAGATGC CTCTGCCGAC       2769
AGTGGTCCCA AGATGGACC CCCACCCACG AGGAGCATCG TGGAAAAAGA AGACGTTCCA        2829
ACCACGTCTT CAAAGCAAGT GGATTGATGT GACATCTCCA CTGACGTAAG GGATGACGCA       2889
CAATCCCACT ATCCTTCGCA AGACCCTTCC TCTATATAAG GAAGTTCATT TCATTTGGAG       2949
AGGACACGCT GAAATCACCA GTCTCTCTCT ATAAATCTAT CTCTCTCTCT ATAACCATGG       3009
AGAAAAAAAT CACTGGATAT ACCACCGTTG ATATATCCCA ATGGCATCGT AAAGAACATT       3069
TTGAGGCATT TCAGTCAGTT GCTCAATGTA CCTATAACCA GACCGTTCAG CTGGATATTA       3129
CGGCCTTTTT AAAGACCGTA AAGAAAAATA AGCACAAGTT TTATCCGGCC TTTATTCACA       3189
TTCTTGCCCG CCTGATGAAT GCTCATCCGG AATTCCGTAT GGCAATGAAA GACGGTGAGC       3249
TGGTGATATG GGATAGTGTT CACCCTTGTT ACACCGTTTT CCATGAGCAA ACTGAAACGT       3309
TTTCATCGCT CTGGAGTGAA TACCACGACG ATTTCCGGCA GTTTCTACAC ATATATTCGC       3369
AAGATGTGGC GTGTTACGGT GAAAACCTGG CCTATTTCCC TAAAGGGTTT ATTGAGAATA       3429
TGTTTTTCGT CTCAGCCAAT CCCTGGGTGA GTTTCACCAG TTTTGATTTA AACGTGGCCA       3489
ATATGGACAA CTTCTTCGCC CCCGTTTTCA CCATGGGCAA ATATTATACG CAAGGCGACA       3549
```

```
AGGTGCTGAT GCCGCTGGCG ATTCAGGTTC ATCATGCCGT CTGTGATGGC TTCCATGTCG    3609

GCAGAATGCT TAATGAATTA CAACAGTACT GCGATGAGTG GCAGGGCGGG GCGTAATTTT    3669

TTTAAGGCAG TTATTGGTGC CCTTAAACGC CTGGTTGCTA CGCCTGAATA AGTGATAATA    3729

AGCGGATGAA TGGCAGAAAT TCGAAAGCAA ATTCGACCCA TCGCGCGTCT AGAGTCCTGC    3789

TTTAATGAGA TATGCGAGAC GCCTATGATC GCATGATATT TGCTTTCAAT TCTGTTGTGC    3849

ACGTTGTAAA AAACCTGAGC ATGTGTAGCT CAGATCCTTA CCGCCGGTTT CGGTTCATTC    3909

TAATGAATAT ATCACCCGTT ACTATCGTAT TTTTATGAAT AATATTCTCC GTTCAATTTA    3969

CTGATTGTAC CCTACTACTT ATATGTACAA TATTAAAATG AAAACAATAT ATTGTGCTGA    4029

ATAGGTTTAT AGCGACATCT ATGATAGAGC GCCACAATAA CAAACAATTG CGTTTTATTA    4089

TTACAAATCC AATTTTAAAA AAAGCGGCAG AACCGGTCAA ACCTAAAAGA CTGATTACAT    4149

AAATCTTATT CAAATTTCAA AAGGCCCCAG GGGCTAGTAT CTACGACACA CCGAGCGGCG    4209

AACTAATAAC GTTCACTGAA GGGAACTCCG GTTCCCCGCC GGCGCGCATG GGTGAGATTC    4269

CTTGAAGTTG AGTATTGGCC GTCCGCTCTA CCGAAAGTTA CGGGCACCAT TCAACCCGGT    4329

CCAGCACGGC GGCCGGGTAA CCGACTTGCT GCCCCGAGAA TTATGCAGCA TTTTTTTGGT    4389

GTATGTGGGC CCCAAATGAA GTGCAGGTCA AACCTTGACA GTGACGACAA ATCGTTGGGC    4449

GGGTCCAGGG CGAATTTTGC GACAACATGT CGAGGCTCAG CAGGACCTGC AGGAATTCGG    4509

CGTAATCATG GTCATAGCTG TTTCCTGTGT GAAATTGTTA TCCGCTCACA ATTCCACACA    4569

ACATACGAGC CGGAAGCATA AAGTGTAAAG CCTGGGGTGC CTAATGAGTG AGCTAACTCA    4629

CATTAATTGC GTTGCGCTCA CTGCCCGCTT TCCAGTCGGG AAACCGTCG TGCCAGCTGC    4689

ATTAATGAAT CGGCCAACGC GCGGGGAGAG GCGGTTTGCG TATTGGGCGC TCTTCCGCTT    4749

CCTCGCTCAC TGACTCGCTG CGCTCGGTCG TTCGGCTGCG GCGAGCGGTA TCAGCTCACT    4809

CAAAGGCGGT AATACGGTTA TCCACAGAAT CAGGGGATAA CGCAGGAAAG AACATGTGAG    4869

CAAAAGGCCA GCAAAAGGCC AGGAACCGTA AAAAGGCCGC GTTGCTGGCG TTTTTCCATA    4929

GGCTCCGCCC CCCTGACGAG CATCACAAAA ATCGACGCTC AAGTCAGAGG TGGCGAAACC    4989

CGACAGGACT ATAAAGATAC CAGGCGTTTC CCCCTGGAAG CTCCCTCGTG CGCTCTCCTG    5049

TTCCGACCCT GCCGCTTACC GGATACCTGT CCGCCTTTCT CCCTTCGGGA AGCGTGGCGC    5109

TTTCTCAATG CTCACGCTGT AGGTATCTCA GTTCGGTGTA GGTCGTTCGC TCCAAGCTGG    5169

GCTGTGTGCA CGAACCCCCC GTTCAGCCCG ACCGCTGCGC CTTATCCGGT AACTATCGTC    5229

TTGAGTCCAA CCCGGTAAGA CACGACTTAT CGCCACTGGC AGCAGCCACT GGTAACAGGA    5289

TTAGCAGAGC GAGGTATGTA GGCGGTGCTA CAGAGTTCTT GAAGTGGTGG CCTAACTACG    5349

GCTACACTAG AAGGACAGTA TTTGGTATCT GCGCTCTGCT GAAGCCAGTT ACCTTCGGAA    5409

AAAGAGTTGG TAGCTCTTGA TCCGGCAAAC AAACCACCGC TGGTAGCGGT GGTTTTTTTG    5469

TTTGCAAGCA GCAGATTACG CGCAGAAAAA AAGGATCTCA AGAAGATCCT TTGATCTTTT    5529

CTACGGGGTC TGACGCTCAG TGGAACGAAA ACTCACGTTA AGGGATTTTG GTCATGAGAT    5589

TATCAAAAAG GATCTTCACC TAGATCCTTT TAAATTAAAA ATGAAGTTTT AAATCAATCT    5649

AAAGTATATA TGAGTAAACT TGGTCTGACA GTTACCAATG CTTAATCAGT GAGGCACCTA    5709

TCTCAGCGAT CTGTCTATTT CGTTCATCCA TAGTTGCCTG ACTCCCCGTC GTGTAGATAA    5769

CTACGATACG GGAGGGCTTA CCATCTGGCC CCAGTGCTGC AATGATACCG CGAGACCCAC    5829

GCTCACCGGC TCCAGATTTA TCAGCAATAA ACCAGCCAGC CGGAAGGGCC GAGCGCAGAA    5889

GTGGTCCTGC AACTTTATCC GCCTCCATCC AGTCTATTAA TTGTTGCCGG GAAGCTAGAG    5949
```

```
TAAGTAGTTC GCCAGTTAAT AGTTTGCGCA ACGTTGTTGC CATTGCTACA GGCATCGTGG    6009

TGTCACGCTC GTCGTTTGGT ATGGCTTCAT TCAGCTCCGG TTCCCAACGA TCAAGGCGAG    6069

TTACATGATC CCCCATGTTG TGCAAAAAAG CGGTTAGCTC CTTCGGTCCT CCGATCGTTG    6129

TCAGAAGTAA GTTGGCCGCA GTGTTATCAC TCATGGTTAT GGCAGCACTG CATAATTCTC    6189

TTACTGTCAT GCCATCCGTA AGATGCTTTT CTGTGACTGG TGAGTACTCA ACCAAGTCAT    6249

TCTGAGAATA GTGTATGCGG CGACCGAGTT GCTCTTGCCC GGCGTCAATA CGGGATAATA    6309

CCGCGCCACA TAGCAGAACT TTAAAAGTGC TCATCATTGG AAAACGTTCT TCGGGGCGAA    6369

AACTCTCAAG GATCTTACCG CTGTTGAGAT CCAGTTCGAT GTAACCCACT CGTGCACCCA    6429

ACTGATCTTC AGCATCTTTT ACTTTCACCA GCGTTTCTGG GTGAGCAAAA ACAGGAAGGC    6489

AAAATGCCGC AAAAAAGGGA ATAAGGGCGA CACGGAAATG TTGAATACTC ATACTCTTCC    6549

TTTTTCAATA TTATTGAAGC ATTTATCAGG GTTATTGTCT CATGAGCGGA TACATATTTG    6609

AATGTATTTA GAAAAATAAA CAAATAGGGG TTCCGCGCAC ATTTCCCCGA AAAGTGCCAC    6669

CTGACGTCTA AGAAACCATT ATTATCATGA CATTAACCTA TAAAAATAGG CGTATCACGA    6729

GGCCCTTTCG TCTCGCGCGT TTCGGTGATG ACGGTGAAAA CCTCTGACAC ATGCAGCTCC    6789

CGGAGACGGT CACAGCTTGT CTGTAAGCGG ATGCCGGGAG CAGACAAGCC CGTCAGGGCG    6849

CGTCAGCGGG TGTTGGCGGG TGTCGGGGCT GGCTTAACTA TGCGGCATCA GAGCAGATTG    6909

TACTGAGAGT GCACCATATG CGGTGTGAAA TACCGCACAG ATGCGTAAGG AGAAAATACC    6969

GCATCAGGCG CCATTCGCCA TTCAGGCTGC GCAACTGTTG GGAAGGGCGA TCGGTGCGGG    7029

CCTCTTCGCT ATTACGCCAG CTGGCGAAAG GGGGATGTGC TGCAAGGCGA TTAAGTTGGG    7089

TAACGCCAGG GTTTTCCCAG TCACGACGTT GTAAAACGAC GGCCAGTAAG CTTGGCTGCA    7149

GGTCGAGATC CACGTGTGGA AGATATGAAT TTTTTTGAGA AACTAGATAA GATTAATGAA    7209

TATCGGTGTT TTGGTTTTTT CTTGTGGCCG TCTTTGTTTA TATTGAGATT TTTCAAATCA    7269

GTGCGCAAGA CGTGACGTAA GTATCTGAGC TAGTTTTTAT TTTTCTACTA ATTTGGTCGT    7329

TTATTTCGGC GTGTAGGACA TGGCAACCGG GCCTGAATTT CGCGGGTATT CTGTTTCTAT    7389

TCCAACTTTT TCTTGATCCG CAGCCATTAA CGACTTTTGA ATAGATACGC TGACACGCCA    7449

AGCCTCGCTA GTCAAAAGTG TACCAAACAA CGCTTTACAG CAAGAACGGA ATGCGCGTGA    7509

CGCTCGCGGT GACGCCATTT CGCCTTTTCA GAAATGGATA AATAGCCTTG CTTCCTATTA    7569

TATCTTCCCA AATTACCAAT ACATTACACT AGCATCTGAA TTTCATAACC AATCTCGATA    7629

CACCAAATCG                                                          7639

(2) INFORMATION FOR SEQ ID NO:23:

(i) SEQUENCE CHARACTERISTICS:
        (A) LENGTH: 7566 base pairs
        (B) TYPE: nucleic acid
        (C) STRANDEDNESS: double
        (D) TOPOLOGY: circular (ii) MOLECULE TYPE: DNA (genomic)

(vi) ORIGINAL SOURCE:
        (A) ORGANISM: plasmid DNA designated as pPS0212

(ix) FEATURE:
        (A) NAME/KEY: CDS
        (B) LOCATION: 1..1785
        (D) OTHER INFORMATION: /note= "Coding region of a
            truncated modified bt2 (cryIAb) gene, also designated as
            the cryIAb6 gene."
```

(ix) FEATURE:
    (A) NAME/KEY: misc_feature
    (B) LOCATION: 1793..2026
    (D) OTHER INFORMATION: /note= "3' regulatory sequence
        containing the polyadenylation site derived from
        Agrobacterium T-DNA gene 7."

(ix) FEATURE:
    (A) NAME/KEY: misc_feature
    (B) LOCATION: 2396..2921
    (D) OTHER INFORMATION: /note= "35S promoter sequence
        derived from Cauliflower mosaic virus."

(ix) FEATURE:
    (A) NAME/KEY: misc_feature
    (B) LOCATION: 2922..3581
    (D) OTHER INFORMATION: /note= "Coding sequence of
        chloramphenicol acetyl transferase gene."

(ix) FEATURE:
    (A) NAME/KEY: misc_feature
    (B) LOCATION: 3582..4407
    (D) OTHER INFORMATION: /note= "3' regulatory sequence
        containing the polyadenylation site derived from
        Agrobacterium T-DNA octopine synthase gene."

(ix) FEATURE:
    (A) NAME/KEY: misc_feature
    (B) LOCATION: 5600..6457
    (D) OTHER INFORMATION: /note= "Sequence complementary to
        the coding sequence of the beta-lactamase gene."

(ix) FEATURE:
    (A) NAME/KEY: misc_feature
    (B) LOCATION: 7071..7566
    (D) OTHER INFORMATION: /note= "TR1' and TR2 promoter
        derived from Agrobacterium T-DNA (with modified leader
        with respect to sequence of pJD884 of SEQ ID NO. 22."

(xi) SEQUENCE DESCRIPTION: SEQ ID NO:23:

```
ATG GCT ATC GAG ACC GGT TAC ACC CCA ATC GAT ATT TCC TTG TCG CTA      48
Met Ala Ile Glu Thr Gly Tyr Thr Pro Ile Asp Ile Ser Leu Ser Leu
 1               5                  10                  15

ACG CAA TTT CTT TTG AGT GAA TTT GTT CCC GGT GCT GGA TTT GTG TTA      96
Thr Gln Phe Leu Leu Ser Glu Phe Val Pro Gly Ala Gly Phe Val Leu
                20                  25                  30

GGA CTA GTT GAT ATA ATA TGG GGA ATT TTT GGT CCC TCT CAA TGG GAC     144
Gly Leu Val Asp Ile Ile Trp Gly Ile Phe Gly Pro Ser Gln Trp Asp
            35                  40                  45

GCA TTT CTT GTA CAA ATT GAA CAG TTA ATT AAC CAA AGA ATA GAA GAA     192
Ala Phe Leu Val Gln Ile Glu Gln Leu Ile Asn Gln Arg Ile Glu Glu
        50                  55                  60

TTC GCT AGG AAC CAA GCC ATT TCT AGA TTA GAA GGA CTA AGC AAT CTT     240
Phe Ala Arg Asn Gln Ala Ile Ser Arg Leu Glu Gly Leu Ser Asn Leu
 65                  70                  75                  80

TAT CAA ATT TAC GCA GAA TCT TTT AGA GAG TGG GAA GCA GAT CCT ACT     288
Tyr Gln Ile Tyr Ala Glu Ser Phe Arg Glu Trp Glu Ala Asp Pro Thr
                85                  90                  95

AAT CCA GCA TTA AGA GAA GAG ATG CGT ATT CAA TTC AAT GAC ATG AAC     336
Asn Pro Ala Leu Arg Glu Glu Met Arg Ile Gln Phe Asn Asp Met Asn
               100                 105                 110

AGT GCC CTT ACA ACC GCT ATT CCT CTT TTT GCA GTT CAA AAT TAT CAA     384
Ser Ala Leu Thr Thr Ala Ile Pro Leu Phe Ala Val Gln Asn Tyr Gln
           115                 120                 125

GTT CCT CTT TTA TCA GTA TAT GTT CAA GCT GCA AAT TTA CAT TTA TCA     432
Val Pro Leu Leu Ser Val Tyr Val Gln Ala Ala Asn Leu His Leu Ser
       130                 135                 140

GTT TTG AGA GAT GTT TCA GTG TTT GGA CAA AGG TGG GGA TTT GAT GCC     480
Val Leu Arg Asp Val Ser Val Phe Gly Gln Arg Trp Gly Phe Asp Ala
145                 150                 155                 160
```

```
GCG ACT ATC AAT AGT CGT TAT AAT GAT TTA ACT AGG CTT ATT GGC AAC     528
Ala Thr Ile Asn Ser Arg Tyr Asn Asp Leu Thr Arg Leu Ile Gly Asn
            165                 170                 175

TAT ACA GAT CAT GCT GTA CGC TGG TAC AAT ACG GGA TTA GAG CGT GTA     576
Tyr Thr Asp His Ala Val Arg Trp Tyr Asn Thr Gly Leu Glu Arg Val
            180                 185                 190

TGG GGA CCG GAT TCT AGA GAC TGG ATC AGG TAC AAC CAG TTC AGG AGG     624
Trp Gly Pro Asp Ser Arg Asp Trp Ile Arg Tyr Asn Gln Phe Arg Arg
            195                 200                 205

GAG TTA ACC CTA ACC GTG TTA GAC ATC GTG TCC CTA TTC CCG AAC TAC     672
Glu Leu Thr Leu Thr Val Leu Asp Ile Val Ser Leu Phe Pro Asn Tyr
    210                 215                 220

GAC AGC AGG ACG TAC CCA ATC CGA ACC GTG TCC CAG TTA ACC AGG GAG     720
Asp Ser Arg Thr Tyr Pro Ile Arg Thr Val Ser Gln Leu Thr Arg Glu
225                 230                 235                 240

ATC TAC ACC AAC CCA GTG TTA GAG AAC TTC GAC GGT AGC TTC CGA GGC     768
Ile Tyr Thr Asn Pro Val Leu Glu Asn Phe Asp Gly Ser Phe Arg Gly
            245                 250                 255

TCG GCT CAG GGC ATC GAG GGA AGC ATC AGG AGC CCA CAC TTG ATG GAC     816
Ser Ala Gln Gly Ile Glu Gly Ser Ile Arg Ser Pro His Leu Met Asp
            260                 265                 270

ATC CTT AAC AGC ATC ACC ATC TAC ACG GAC GCT CAC AGG GGA GAG TAC     864
Ile Leu Asn Ser Ile Thr Ile Tyr Thr Asp Ala His Arg Gly Glu Tyr
            275                 280                 285

TAC TGG TCC GGG CAC CAG ATC ATG GCT TCC CCT GTG GGG TTC TCG GGG     912
Tyr Trp Ser Gly His Gln Ile Met Ala Ser Pro Val Gly Phe Ser Gly
            290                 295                 300

CCA GAA TTC ACT TTT CCG CTA TAT GGA ACT ATG GGA AAT GCA GCT CCA     960
Pro Glu Phe Thr Phe Pro Leu Tyr Gly Thr Met Gly Asn Ala Ala Pro
305                 310                 315                 320

CAA CAA CGT ATT GTT GCT CAA CTA GGT CAG GGC GTG TAT AGA ACA TTA    1008
Gln Gln Arg Ile Val Ala Gln Leu Gly Gln Gly Val Tyr Arg Thr Leu
            325                 330                 335

TCG TCC ACT TTA TAT AGA AGA CCT TTT AAT ATA GGG ATA AAT AAT CAA    1056
Ser Ser Thr Leu Tyr Arg Arg Pro Phe Asn Ile Gly Ile Asn Asn Gln
            340                 345                 350

CAA CTA TCT GTT CTT GAC GGG ACA GAA TTT GCT TAT GGA ACC TCC TCA    1104
Gln Leu Ser Val Leu Asp Gly Thr Glu Phe Ala Tyr Gly Thr Ser Ser
            355                 360                 365

AAT TTG CCA TCC GCT GTA TAC AGA AAA AGC GGA ACG GTA GAT TCG CTG    1152
Asn Leu Pro Ser Ala Val Tyr Arg Lys Ser Gly Thr Val Asp Ser Leu
370                 375                 380

GAT GAA ATA CCG CCA CAG AAT AAC AAC GTG CCA CCT AGG CAA GGA TTT    1200
Asp Glu Ile Pro Pro Gln Asn Asn Asn Val Pro Pro Arg Gln Gly Phe
385                 390                 395                 400

AGT CAT CGA TTA AGC CAT GTT TCA ATG TTT CGT TCA GGC TTT AGT AAT    1248
Ser His Arg Leu Ser His Val Ser Met Phe Arg Ser Gly Phe Ser Asn
            405                 410                 415

AGT AGT GTA AGT ATA ATA AGA GCT CCT ATG TTC TCT TGG ATA CAT CGT    1296
Ser Ser Val Ser Ile Ile Arg Ala Pro Met Phe Ser Trp Ile His Arg
            420                 425                 430

AGT GCT GAA TTT AAT AAT ATA ATT CCT TCA TCA CAA ATT ACA CAA ATA    1344
Ser Ala Glu Phe Asn Asn Ile Ile Pro Ser Ser Gln Ile Thr Gln Ile
            435                 440                 445

CCT TTA ACA AAA TCT ACT AAT CTT GGC TCT GGA ACT TCT GTC GTT AAA    1392
Pro Leu Thr Lys Ser Thr Asn Leu Gly Ser Gly Thr Ser Val Val Lys
450                 455                 460

GGA CCA GGA TTT ACA GGA GGA GAT ATT CTT CGA AGA ACT TCA CCT GGC    1440
Gly Pro Gly Phe Thr Gly Gly Asp Ile Leu Arg Arg Thr Ser Pro Gly
465                 470                 475                 480
```

-continued

```
CAG ATT TCA ACC TTA AGA GTA AAT ATT ACT GCA CCA TTA TCA CAA AGA      1488
Gln Ile Ser Thr Leu Arg Val Asn Ile Thr Ala Pro Leu Ser Gln Arg
                485                 490                 495

TAT CGG GTA AGA ATT CGC TAC GCT TCT ACC ACA AAT TTA CAA TTC CAT      1536
Tyr Arg Val Arg Ile Arg Tyr Ala Ser Thr Thr Asn Leu Gln Phe His
            500                 505                 510

ACA TCA ATT GAC GGA AGA CCT ATT AAT CAG GGG AAT TTT TCA GCA ACT      1584
Thr Ser Ile Asp Gly Arg Pro Ile Asn Gln Gly Asn Phe Ser Ala Thr
        515                 520                 525

ATG AGT AGT GGG AGT AAT TTA CAG TCC GGA AGC TTT AGG ACT GTA GGT      1632
Met Ser Ser Gly Ser Asn Leu Gln Ser Gly Ser Phe Arg Thr Val Gly
    530                 535                 540

TTT ACT ACT CCG TTT AAC TTT TCA AAT GGA TCA AGT GTA TTT ACG TTA      1680
Phe Thr Thr Pro Phe Asn Phe Ser Asn Gly Ser Ser Val Phe Thr Leu
545                 550                 555                 560

AGT GCT CAT GTC TTC AAT TCA GGC AAT GAA GTT TAT ATA GAT CGA ATT      1728
Ser Ala His Val Phe Asn Ser Gly Asn Glu Val Tyr Ile Asp Arg Ile
                565                 570                 575

GAA TTT GTT CCG GCA GAA GTA ACC TTC GAC CTG CAG CCA AGC TTG CTG      1776
Glu Phe Val Pro Ala Glu Val Thr Phe Asp Leu Gln Pro Ser Leu Leu
            580                 585                 590

ATT GAT TGA CCGGATCGAT CCGGCTCTAG CAGATCCCCC GATGAGCTAA              1825
Ile Asp *
        595

GCTAGCTATA TCATCAATTT ATGTATTACA CATAATATCG CACTCAGTCT TTCATCTACG    1885

GCAATGTACC AGCTGATATA ATCAGTTATT GAAATATTTC TGAATTTAAA CTTGCATCAA    1945

TAAATTTATG TTTTTGCTTG GACTATAATA CCTGACTTGT TATTTTATCA ATAAATATTT    2005

AAACTATATT TCTTTCAAGA TGGGAATTAA CATCTACAAA TTGCCTTTTC TTATCGACCA    2065

TGTACGGGTA CCGAGCTCGA ATTCCTACGC AGCAGGTCTC ATCAAGACGA TCTACCCGAG    2125

TAACAATCTC CAGGAGATCA AATACCTTCC CAAGAAGGTT AAAGATGCAG TCAAAAGATT    2185

CAGGACTAAT TGCATCAAGA ACACAGAGAA AGACATATTT CTCAAGATCA GAAGTACTAT    2245

TCCAGTATGG ACGATTCAAG GCTTGCTTCA TAAACCAAGG CAAGTAATAG AGATTGGAGT    2305

CTCTAAAAAG GTAGTTCCTA CTGAATCTAA GGCCATGCAT GGAGTCTAAG ATTCAAATCG    2365

AGGATCTAAC AGAACTCGCC GTGAAGACTG GCGAACAGTT CATACAGAGT CTTTTACGAC    2425

TCAATGACAA GAAGAAAATC TTCGTCAACA TGGTGGAGCA CGACACTCTG GTCTACTCCA    2485

AAAATGTCAA AGATACAGTC TCAGAAGACC AAAGGGCTAT TGAGACTTTT CAACAAAGGA    2545

TAATTTCGGG AAACCTCCTC GGATTCCATT GCCCAGCTAT CTGTCACTTC ATCGAAAGGA    2605

CAGTAGAAAA GGAAGGTGGC TCCTACAAAT GCCATCATTG CGATAAAGGA AAGGCTATCA    2665

TTCAAGATGC CTCTGCCGAC AGTGGTCCCA AGATGGACC CCCACCCACG AGGAGCATCG     2725

TGGAAAAAGA AGACGTTCCA ACCACGTCTT CAAAGCAAGT GGATTGATGT GACATCTCCA    2785

CTGACGTAAG GGATGACGCA CAATCCCACT ATCCTTCGCA AGACCCTTCC TCTATATAAG    2845

GAAGTTCATT TCATTTGGAG AGGACACGCT GAAATCACCA GTCTCTCTCT ATAAATCTAT    2905

CTCTCTCTCT ATAACCATGG AGAAAAAAAT CACTGGATAT ACCACCGTTG ATATATCCCA    2965

ATGGCATCGT AAAGAACATT TTGAGGCATT TCAGTCAGTT GCTCAATGTA CCTATAACCA    3025

GACCGTTCAG CTGGATATTA CGGCCTTTTT AAAGACCGTA AAGAAAAATA AGCACAAGTT    3085

TTATCCGGCC TTTATTCACA TTCTTGCCCG CCTGATGAAT GCTCATCCGG AATTCCGTAT    3145

GGCAATGAAA GACGGTGAGC TGGTGATATG GGATAGTGTT CACCCTTGTT ACACCGTTTT    3205

CCATGAGCAA ACTGAAACGT TTTCATCGCT CTGGAGTGAA TACCACGACG ATTTCCGGCA    3265
```

```
GTTTCTACAC ATATATTCGC AAGATGTGGC GTGTTACGGT GAAAACCTGG CCTATTTCCC    3325

TAAAGGGTTT ATTGAGAATA TGTTTTTCGT CTCAGCCAAT CCCTGGGTGA GTTTCACCAG    3385

TTTTGATTTA AACGTGGCCA ATATGGACAA CTTCTTCGCC CCCGTTTTCA CCATGGGCAA    3445

ATATTATACG CAAGGCGACA AGGTGCTGAT GCCGCTGGCG ATTCAGGTTC ATCATGCCGT    3505

CTGTGATGGC TTCCATGTCG GCAGAATGCT TAATGAATTA CAACAGTACT GCGATGAGTG    3565

GCAGGGCGGG GCGTAATTTT TTTAAGGCAG TTATTGGTGC CCTTAAACGC CTGGTTGCTA    3625

CGCCTGAATA AGTGATAATA AGCGGATGAA TGGCAGAAAT TCGAAAGCAA ATTCGACCCA    3685

TCGCGCGTCT AGAGTCCTGC TTTAATGAGA TATGCGAGAC GCCTATGATC GCATGATATT    3745

TGCTTTCAAT TCTGTTGTGC ACGTTGTAAA AAACCTGAGC ATGTGTAGCT CAGATCCTTA    3805

CCGCCGGTTT CGGTTCATTC TAATGAATAT ATCACCCGTT ACTATCGTAT TTTTATGAAT    3865

AATATTCTCC GTTCAATTTA CTGATTGTAC CCTACTACTT ATATGTACAA TATTAAAATG    3925

AAAACAATAT ATTGTGCTGA ATAGGTTTAT AGCGACATCT ATGATAGAGC GCCACAATAA    3985

CAAACAATTG CGTTTATTA TTACAAATCC AATTTTAAAA AAAGCGGCAG AACCGGTCAA    4045

ACCTAAAAGA CTGATTACAT AAATCTTATT CAAATTTCAA AAGGCCCCAG GGGCTAGTAT    4105

CTACGACACA CCGAGCGGCG AACTAATAAC GTTCACTGAA GGGAACTCCG GTTCCCCGCC    4165

GGCGCGCATG GGTGAGATTC CTTGAAGTTG AGTATTGGCC GTCCGCTCTA CCGAAAGTTA    4225

CGGGCACCAT TCAACCCGGT CCAGCACGGC GGCCGGGTAA CCGACTTGCT GCCCCGAGAA    4285

TTATGCAGCA TTTTTTTGGT GTATGTGGGC CCCAAATGAA GTGCAGGTCA AACCTTGACA    4345

GTGACGACAA ATCGTTGGGC GGGTCCAGGG CGAATTTTGC GACAACATGT CGAGGCTCAG    4405

CAGGACCTGC AGGAATTCGG CGTAATCATG GTCATAGCTG TTTCCTGTGT GAAATTGTTA    4465

TCCGCTCACA ATTCCACACA ACATACGAGC CGGAAGCATA AAGTGTAAAG CCTGGGGTGC    4525

CTAATGAGTG AGCTAACTCA CATTAATTGC GTTGCGCTCA CTGCCCGCTT TCCAGTCGGG    4585

AAACCTGTCG TGCCAGCTGC ATTAATGAAT CGGCCAACGC GCGGGGAGAG GCGGTTTGCG    4645

TATTGGGCGC TCTTCCGCTT CCTCGCTCAC TGACTCGCTG CGCTCGGTCG TTCGGCTGCG    4705

GCGAGCGGTA TCAGCTCACT CAAAGGCGGT AATACGGTTA TCCACAGAAT CAGGGGATAA    4765

CGCAGGAAAG AACATGTGAG CAAAAGGCCA GCAAAAGGCC AGGAACCGTA AAAAGGCCGC    4825

GTTGCTGGCG TTTTTCCATA GGCTCCGCCC CCCTGACGAG CATCACAAAA ATCGACGCTC    4885

AAGTCAGAGG TGGCGAAACC CGACAGGACT ATAAAGATAC CAGGCGTTTC CCCCTGGAAG    4945

CTCCCTCGTG CGCTCTCCTG TTCCGACCCT GCCGCTTACC GGATACCTGT CCGCCTTTCT    5005

CCCTTCGGGA AGCGTGGCGC TTTCTCAATG CTCACGCTGT AGGTATCTCA GTTCGGTGTA    5065

GGTCGTTCGC TCCAAGCTGG GCTGTGTGCA CGAACCCCCC GTTCAGCCCG ACCGCTGCGC    5125

CTTATCCGGT AACTATCGTC TTGAGTCCAA CCCGGTAAGA CACGACTTAT CGCCACTGGC    5185

AGCAGCCACT GGTAACAGGA TTAGCAGAGC GAGGTATGTA GGCGGTGCTA CAGAGTTCTT    5245

GAAGTGGTGG CCTAACTACG GCTACACTAG AAGGACAGTA TTTGGTATCT GCGCTCTGCT    5305

GAAGCCAGTT ACCTTCGGAA AAAGAGTTGG TAGCTCTTGA TCCGGCAAAC AAACCACCGC    5365

TGGTAGCGGT GGTTTTTTTG TTTGCAAGCA GCAGATTACG CGCAGAAAAA AAGGATCTCA    5425

AGAAGATCCT TTGATCTTTT CTACGGGGTC TGACGCTCAG TGGAACGAAA ACTCACGTTA    5485

AGGGATTTTG GTCATGAGAT TATCAAAAAG GATCTTCACC TAGATCCTTT TAAATTAAAA    5545

ATGAAGTTTT AAATCAATCT AAAGTATATA TGAGTAAACT TGGTCTGACA GTTACCAATG    5605

CTTAATCAGT GAGGCACCTA TCTCAGCGAT CTGTCTATTT CGTTCATCCA TAGTTGCCTG    5665
```

-continued

```
ACTCCCCGTC GTGTAGATAA CTACGATACG GGAGGGCTTA CCATCTGGCC CCAGTGCTGC      5725

AATGATACCG CGAGACCCAC GCTCACCGGC TCCAGATTTA TCAGCAATAA ACCAGCCAGC      5785

CGGAAGGGCC GAGCGCAGAA GTGGTCCTGC AACTTTATCC GCCTCCATCC AGTCTATTAA      5845

TTGTTGCCGG GAAGCTAGAG TAAGTAGTTC GCCAGTTAAT AGTTTGCGCA ACGTTGTTGC      5905

CATTGCTACA GGCATCGTGG TGTCACGCTC GTCGTTTGGT ATGGCTTCAT TCAGCTCCGG      5965

TTCCCAACGA TCAAGGCGAG TTACATGATC CCCCATGTTG TGCAAAAAAG CGGTTAGCTC      6025

CTTCGGTCCT CCGATCGTTG TCAGAAGTAA GTTGGCCGCA GTGTTATCAC TCATGGTTAT      6085

GGCAGCACTG CATAATTCTC TTACTGTCAT GCCATCCGTA AGATGCTTTT CTGTGACTGG      6145

TGAGTACTCA ACCAAGTCAT TCTGAGAATA GTGTATGCGG CGACCGAGTT GCTCTTGCCC      6205

GGCGTCAATA CGGGATAATA CCGCGCCACA TAGCAGAACT TTAAAAGTGC TCATCATTGG      6265

AAAACGTTCT TCGGGGCGAA AACTCTCAAG GATCTTACCG CTGTTGAGAT CCAGTTCGAT      6325

GTAACCCACT CGTGCACCCA ACTGATCTTC AGCATCTTTT ACTTTCACCA GCGTTTCTGG      6385

GTGAGCAAAA ACAGGAAGGC AAAATGCCGC AAAAAAGGGA ATAAGGGCGA CACGGAAATG      6445

TTGAATACTC ATACTCTTCC TTTTTCAATA TTATTGAAGC ATTTATCAGG GTTATTGTCT      6505

CATGAGCGGA TACATATTTG AATGTATTTA GAAAAATAAA CAAATAGGGG TTCCGCGCAC      6565

ATTTCCCCGA AAAGTGCCAC CTGACGTCTA AGAAACCATT ATTATCATGA CATTAACCTA      6625

TAAAAATAGG CGTATCACGA GGCCCTTTCG TCTCGCGCGT TTCGGTGATG ACGGTGAAAA      6685

CCTCTGACAC ATGCAGCTCC CGGAGACGGT CACAGCTTGT CTGTAAGCGG ATGCCGGGAG      6745

CAGACAAGCC CGTCAGGGCG CGTCAGCGGG TGTTGGCGGG TGTCGGGGCT GGCTTAACTA      6805

TGCGGCATCA GAGCAGATTG TACTGAGAGT GCACCATATG CGGTGTGAAA TACCGCACAG      6865

ATGCGTAAGG AGAAAATACC GCATCAGGCG CCATTCGCCA TTCAGGCTGC GCAACTGTTG      6925

GGAAGGGCGA TCGGTGCGGG CCTCTTCGCT ATTACGCCAG CTGGCGAAAG GGGGATGTGC      6985

TGCAAGGCGA TTAAGTTGGG TAACGCCAGG GTTTTCCCAG TCACGACGTT GTAAAACGAC      7045

GGCCAGTAAG CTTGGCTGCA GGTCGAGATC CACGTGTGGA AGATATGAAT TTTTTTGAGA      7105

AACTAGATAA GATTAATGAA TATCGGTGTT TTGGTTTTTT CTTGTGGCCG TCTTTGTTTA      7165

TATTGAGATT TTTCAAATCA GTGCGCAAGA CGTGACGTAA GTATCTGAGC TAGTTTTTAT      7225

TTTTCTACTA ATTTGGTCGT TTATTTCGGC GTGTAGGACA TGGCAACCGG GCCTGAATTT      7285

CGCGGGTATT CTGTTTCTAT TCCAACTTTT TCTTGATCCG CAGCCATTAA CGACTTTTGA      7345

ATAGATACGC TGACACGCCA AGCCTCGCTA GTCAAAAGTG TACCAAACAA CGCTTTACAG      7405

CAAGAACGGA ATGCGCGTGA CGCTCGCGGT GACGCCATTT CGCCTTTTCA GAAATGGATA      7465

AATAGCCTTG CTTCCTATTA TATCTTCCCA AATTACCAAT ACATTACACT AGCATCTGAA      7525

TTTCATAACC AATCTCGATA CACCAAATCG GTACCAAAAC C                         7566
```

MODIFIED *BACILLUS THURINGIENSIS* GENES WITH IMPROVED EXPRESSION IN PLANT CELLS, METHODS OF PRODUCTION ON AND USE

This invention provides a modified gene, such as a *Bacillus thuringiensis* ("Bt") gene (the "modified Bt ICP gene") encoding all or an insecticidally-effective portion of a Bt insecticidal crystal protein ("ICP"). A plant, transformed with the modified gene, shows higher expression levels of the encoded protein.

BACKGROUND OF THE INVENTION

Plant genetic engineering technology has made significant progress during the last 10 years. It has become possible to introduce stably foreign genes into plants. This has provided exciting opportunities for modern agriculture. Derivatives of the Ti-plasmid of the plant pathogen, *Agrobacterium tumefaciens,* have proven to be efficient and highly versatile vehicles for the introduction of foreign genes into plants and plant cells. In addition, a variety of free DNA delivery methods, such as electroporation, microinjection, pollen-mediated gene transfer and particle gun technology, have been developed for the same purpose.

The major aim of plant transformations by genetic engineering has been crop improvement. In an initial phase, research has been focussed on the engineering into plants of useful traits such as insect-resistance. In this respect, progress in engineering insect resistance in transgenic plants has been obtained through the use of genes, encoding ICPs, from Bt strains (Vaeck et al, 1987). A Bt strain is a spore forming gram-positive bacterium that produces a parasporal crystal which is composed of crystal proteins which are specifically toxic against insect larvae. Bt ICPs possess a specific insecticidal spectrum and display no toxicity towards other animals and humans (Gasser and Fraley, 1989). Therefore, the Bt ICP genes are highly suited for plant engineering purposes.

For more than 20 years, Bt crystal spore preparations have been used as biological insecticides. The commercial use of Bt sprays has however been limited by high production costs and the instability of crystal proteins When exposed in the field (Vaeck et al, 1987). The heterogeneity of Bt strains has been well documented. Strains active against Lepidoptera (Dulmage et al, 1981), Diptera (Goldberg and Margalit, 1977) and Coleoptera (Krieg et al, 1983) have been described.

Bt strains produce endogenous crystals upon sporulation. Upon ingestion by insect larvae, the crystals are solubilzed in the alkaline environment of the insect midgut giving rise to a protoxin which is subsequently proteolytically converted into a toxic core fragment or toxin of 60–70 Kda. The toxin causes cytolysis of the epithelial midgut cells. The specificity of Bt ICPs can be determined by their interaction with high-affinity binding sites present on insects' midgut epithelia.

The identification of Bt ICPs and the cloning and sequencing of Bt ICP genes has been reviewed by Höfte and Whiteley (1989). The Bt ICP genes share a number of common properties. They generally encode insecticidal proteins of 130 kDa to 140 kDa or of about 70 kDa, which contain toxic fragments of 60±10 kDa (Höfte and Whiteley, 1989). The Bt ICP genes have been classified into four major groups according to both their structural similarities and insecticidal spectra (Höfte and Whiteley, 1989): Lepidoptera-specific (CryI), Lepidoptera- and Diptera-specific (CryII), Coleoptera-specific (CryIII) and Diptera-specific (CryIV) genes. The Lepidoptera-specific genes (CryI) all encode 130–140 kDa proteins. These proteins are generally synthesized as protoxins. The toxic domain is localized in the N-terminal half of the protoxin. Deletion analysis of several CryI genes confirm that 3' portions of the protoxins are not absolutely required for toxic activity (Schnepf et al, 1985). CryII genes encode 65 kDa proteins (Widner and Whiteley, 1985). The CryIIA proteins are toxic against both Lepidoptera and Diptera while the CryIIB proteins are toxic only to Lepidopteran insects. The Coleoptera-specific genes (CryIII) generally encode proteins with a molecular weight of about 70 kDa (Höfte and Whiteley, 1989). The CryIIIA gene expressed in *E. coli* directs the synthesis of a 72 kDa protein which is toxic for the Colorado potato beetle. This 72 kDa protein is processed to a 66 kDa protein by spore-associated bacterial proteases which remove the first 57 N-terminal amino acids (McPherson et al, 1988). Deletion analysis demonstrated that this type of gene cannot be truncated at its 3'-end without the loss of toxic activity (Höfte and Whiteley, 1989). Recently an anti-coleopteran strain, which produces a 130 kDa protein, has also been described (European patent application ("EPA") 89400428.2). The CryIV class of crystal protein genes is composed of a heterogeneous group of Diptera-specific crystal protein genes (Höfte and Whiteley, 1989).

The feasibility of generating insect-resistant transgenic crops by using Bt ICPs has been demonstrated (Vaeck et al, 1987; Fischhoff et al, 1987 and Barton et al, 1987). Transgenic plants offer an attractive alternative and provide an entirely new approach to insect control in agriculture which is at the same time safe, environmentally attractive and cost-effective (Meeusen and Warren, 1989). Successful insect control has been observed under field conditions (Delannay et al, 1989; Meeusen and Warren, 1989).

In all cases, Agrobacterium-mediated gene transfer has been used to express chimeric Bt ICP genes in plants (Vaeck et al, 1987; Barton et al, 1987; Fischhoff et al, 1987). Bt ICP genes were placed under the control of a strong promoter capable of directing gene expression in plant cells. It is however remarkable that expression levels in plant cells were high enough only to obtain insect-killing levels of Bt ICP genes when truncated genes were used (Vaeck et al, 1987; Barton et al, 1987). None of the transgenic plants containing a full-length Bt ICP gene produced insect-killing activity. Moreover, Barton et al. (1987) showed that tobacco calli transformed with the entire Bt ICP coding region became necrotic and died. These results indicate that the Bt ICP gene presents unusual problems that must be overcome to obtain significant levels of expression in plants. Even when using a truncated Bt ICP gene for plant transformation, the steady state levels of Bt ICP mRNA obtained in transgenic plants are very low relative to levels produced by both an adjacent NPT II-gene, used as a marker, and by other chimeric genes (Barton et al, 1987; Vaeck et al, 1987). Moreover, the Bt ICP full size mRNA cannot be detected by Northern blot analysis. Similar observations were made by Fischhoff et al. (1987); they reported that the level of Bt ICP mRNA was much lower than expected for a chimeric gene expressed from the CaMV35S promoter. In other words, the cytoplasmic accumulation of the Bt mRNA, and consequently the expression of the Bt ICP protein in plant cells, are extremely inefficient. By contrast, in microorganisms, it has been shown that truncated Bt ICP genes are less favorable than full-length genes (Adang et al, 1985), indicating that the inefficient expression is solely related to the heterologous expression of Bt ICP genes in plants.

The problem of obtaining significant Bt ICP expression levels in plant cells seems to be inherent and intrinsic to the wild-type Bt ICP genes. Furthermore, the relatively low and poor expression levels obtained in plants appears to be a common phenomenon for all Bt ICP genes.

It is known that there are six steps at which gene expression can be controlled neucaryotes (Darnell, 1982):

1) Transcriptional control
2) RNA processing control
3) RNA transport control
4) mRNA degradation control
5) translational control
6) protein activity control For all genes, transcriptional control is considered to be of paramount importance (The Molecular Biology of the Cell, 1989).

In European patent publications ("EP") 385,962 and 359,472 efforts to modify the codon usage of Bt ICP genes to improve their expressions in plant cells have been reported. However, wholesale (i.e., non-selective) changes in codon usage can introduce cryptic regulatory signals in a gene, thereby causing problems in one or more of the six steps mentioned above for gene expression, and thus inhibiting or interfering with transcription and/or translation of the modified foreign gene in plant cells. For example, changes in codon usage can cause differential rates of mRNA production, producing instability in the mRNA, so produced (e.g., by exposure of regions of the mRNA, unprotected by ribosomes, to attack and degradation by cytoplasmic enzymes). Changes in codon usage also can inadvertantly interfere with expression of the so-modified gene. EP 359,472 suggests that plant consensus splice sites, if present in the native Bt tenebrionis coding region, be modified so as to eliminate potentially deleterious sequences.

PCT patent publication WO 91/16432 describes the slow rate and/or level of nuclear production of a Bt ICP mRNA as an important cause of the relatively low expression levels of Bt ICP genes in plant cells. In particular, RNA polymerase elongation was found to be hindered in a specific region of the genes.

SUMMARY OF THE INVENTION

In accordance with this invention is provided a process for modifying a gene, preferably a Bt ICP gene, particularly a cryI gene, quite particularly a cryIAb gene, whose level and/or rate of expression in a plant cell, transformed with the gene, is limited by the rate and/or level of nuclear production of a full length (i.e. unspliced) mRNA encoded by the gene; the process comprises the following step:

inactivating, preferably destroying or removing, in the coding region of the gene, at least one of the following process-directing sequence elements:

i) a cryptic promoter, such as a minimal promoter, in either a sense or anti-sense orientation, which can direct site-specific transcription initiation in the plant cell by partial or complete assembly of an RNA polymerase II initiation complex; particularly a cryptic promoter containing at least one DNA regulatory element such as a CCAAT sequence or a TATA sequence, or, ii) a DNA encoding an abortive intron that, at the RNA level, causes entry of a precursor mRNA species in a splicing pathway, the precursor mRNA species being processed in such a way that the resulting mRNA species does not accumulate substantially in the cytoplasm of the plant cell;

the process-directing sequence elements preferably being inactivated by introducing translationally neutral modifications in the coding region of the gene by:

a) introducing DNA encoding an intron, known to be efficiently spliced in the plant cell, and/or b) changing amino acid codons with others encoding the same amino acids.

Also in accordance with this invention is provided a gene to be used to transform a plant cell, preferably a Bt ICP gene, particularly a cryI gene, quite particularly a cryIAb gene, that is modified by the process of this invention (a "modified gene").

Further in accordance with this invention, a process is provided for improving the properties, e.g. insect resistance, of a plant by transforming the plant cell genome with at least one modified gene.

This invention also relates to a chimeric gene which can be used to transform plant cells and which contains the following operably-linked DNA fragments in the same transcriptional unit:

1) the coding region of the modified gene;

2) a promoter suitable for directing transcription of the modified gene in the plant cells; and 3) suitable transcript 3' end formation and polyadenylation signals for expressing the modified gene in the plant cells.

This invention further relates to:

a cell of a plant, the nuclear genome of which has been transformed to contain, preferably stably integrated therein, the modified gene particularly the chimeric gene;

cell cultures consisting of the plant cell;

a plant which is regenerated from the transformed plant cell or is produced from the so-regenerated plant, the genome of which contains the modified gene, particularly the chimeric gene, and which shows improved properties, e.g., resistance to insect pests;

seeds of the plant; and a vector for stably transforming the nuclear genome of plant cells with the modified gene, particularly the chimeric gene.

BRIEF DESCRIPTION OF THE DRAWINGS

FIG. 1 is a comparison of the transcriptional activity of neo and bt884 genes in nuclei of N28-220 of Example 1;

FIG. 2 is a schematic representation of the DMS footprint of the bt884 coding region between nucleotides 668 and 834.

FIG. 3A is a schematic view of the bt884 coding region with four PCR primer sets of Example 4.

FIG. 3B is schematic views of three DNA fragments (I, II and III) obtained by PCR reactions with primers PS58 and PS59.

DETAILED DESCRIPTION OF THE INVENTION

"Gene" as used herein means a DNA sequence encoding a protein, preferably a Bt ICP. This includes a modified or synthetic DNA sequence, as well as a naturally occurring DNA sequence, encoding a protein.

"Coding region" as used herein means that part of a gene that specifies the amino acid sequence of a protein. In general, a coding region comprises a plurality of translational codons that correspond to the translated part of the fully processed mRNA.

"Bt ICP gene" as used herein means a DNA sequence encoding a Bt ICP which is derived directly or indirectly from *B. thuringiensis*. This includes a modified, a synthetic or a naturally occurring DNA sequence, encoding a Bt ICP.

As used herein, "truncated Bt gene" should be understood as a fragment of a full-length Bt gene which still encodes at least the toxic part of the Bt ICP, preferentially the toxin.

As used herein, "Bt ICP" should be understood as an intact protein which can be produced in nature by *B. thuringiensis* or a part or derivative of such a protein which has insecticidal activity. A Bt ICP can be a protoxin, as well as an active toxin or other insecticidal truncated part of a protoxin which need not be crystalline and which need not be a naturally occurring protein. An example of a Bt ICP is a Bt2 insecticidal crystal protein (Höfte et al, 1986; the terminology of Bt2 is according to Höfte and Whiteley (1989) "CryIAb"), as well as its insecticidally effective parts which are truncated at its C- and/or N-terminal ends towards its trypsin cleavage site(s) and preferably having a molecular weight of 60–80 kDa. Other examples of Bt ICPs are: lepidopteran-active ICPs like Bt3, Bt4, Bt14, Bt15, Bt18, Bt73, cryIG described in Gleave et al 1992), cryIF described in EP 405,810; and coleopteran-active ICPs like: Bt13, Bt21, Bt22, BtI260 and BtI109P as disclosed in PCT publications WO 90/15139 and WO 90/09445, in Höfte and Whiteley (1989) and in EPA 90403724.9, or any modified or hybrid ICPs having insecticidal activity.

As used herein, "protoxin" should be understood as the primary translation product of a full-length gene encoding a Bt ICP.

As used herein, "toxin" or "active toxin" or "toxic core" should all be understood as a part of a protoxin which has insecticidal activity and which can for instance be obtained by protease (e.g. by trypsin) cleavage.

As used herein, a "process-directing sequence element" is a genetically cis-acting regulatory element that is either a DNA encoding an abortive intron or is a cryptic promoter whose presence in the coding region of a gene in a plant cell substantially inhibits or prevents the gene's transcription to a full length mRNA, the nuclear accumulation of a full length mRNA and/or the nuclear export of a full length mRNA. Such a sequence element can be different from known plant promoters or plant introns in a given plant cell. A process-directing sequence element would, if not inactivated, actually be recognized by a plant cell and thereby would interfere with gene expression in the plant cell. A genetically cis-acting regulatory element of this invention is believed to be involved in, and/or responsible for, a gene expression-controlling step, such as is listed in the Background of the Invention, that interferes with gene, particularly Bt ICP gene, expression in plant cells.

A "cryptic promoter", such as a "minimal promoter", as used herein means a DNA sequence which is located within the coding region of a protein-encoding gene in either a sense or anti-sense orientation and which can direct site-specific transcription initiation in a given plant cell by partial or complete assembly of an RNA polymerase II initiation complex. Such cryptic promoters are believed to be active due to the presence of so-called "DNA regulatory elements" which are cis-acting, such as the CCAAT and TATA sequences, which specifically interact with nuclear factors. It appears that a cryptic promoter interferes with gene expression by interacting with nuclear proteins and thereby causing transcriptional interference to RNA polymerase II transcribing the gene, or by being transcriptionally active and thereby specifying, depending on its orientation within the gene, a sense or anti-sense RNA, causing sense or anti-sense suppression of gene expression.

A "DNA regulatory element" herein is a sequence in a promoter region that is involved in the partial or complete assembly of an RNA polymerase II initiation complex. Known examples of such DNA regulatory elements are the TATA box and the CCAAT box (Ha and An, 1989; Paul et al, 1987), which in many plant promoters are separated by about 20 to 50 nucleotides, with the TATA box being located about 32±7 nucleotides upstream from the transcription initiation site (Joshi, 1987). Other known DNA regulatory elements are, for example, those listed by Katagiri and Chua (1992).

A "precursor mRNA" or "pre-mRNA" refers to the protein-encoding RNA that is transcribed from the DNA in the nucleus of a plant cell. A pre-mRNA can be further processed, for instance by the removal of plant introns, and the fully-processed or mature mRNA is ultimately translated in the cytoplasm of the plant cell. As used herein a "full length mRNA", a "fully processed mRNA", or a "mature mRNA" is an mRNA that can be translated in the cytoplasm and encodes the protein encoded by the gene.

"Abortive splicing" as used herein is a process in which a precursor mRNA species enters a splicing pathway of a plant cell and is processed in such a way that the spliced mRNA does not accumulate substantially in the plant cell cytoplasm, e.g. the mRNA decays during or after splicing in the nucleus before transport to the cytoplasm or it decays rapidly in the cytoplasm. It appears that in abortive splicing, only a relatively small number of the pre-mRNAs are effectively processed with removal of an intron and subsequent junction of the exon, whereby only the actually spliced mRNAs are detectable in some or all plant cells. Abortive splicing should not be confused with partially active splicing in which a majority of the pre-mRNAs which enter the splicing pathway are effectively spliced, but with only a low frequency of such pre-mRNAs actually entering the splicing pathway.

An "abortive intron" is any RNA sequence which is present in a pre-mRNA and which is removed when the pre-mRNA is abortively spliced in a plant cell. A gene may encode more than one abortive intron, and it is believed that abortive splicing thereof is part of an ordered process with dominant intron(s) being spliced out first and with less dominant introns being spliced out later in a plant cell.

"Abortive intron splice sites" as used herein are those nicking sites at the 5' and 3' sides of an abortive intron at which splicing occurs in any pre-mRNA that is abortively spliced.

In accordance with this invention, a cryptic promoter in the coding region of a particular gene, preferably a Bt ICP gene, can be detected by the following procedure:

In a first step a region (the "pausing region") is identified in the gene where transcription elongation is substantially inhibited. Pausing is the process by which the elongation rate of RNA polymerase II, active in transcription, reduces. Pausing differs from termination in that RNA polymerase II remains associated to the template and can resume RNA synthesis. A pausing region in a transcription unit can be determined by measuring the transcriptional activity of RNA polymerase II complexes transcribing the gene, for example by run-on analysis as described in PCT patent publication WO 91/16432, for consecutive, partially overlapping regions of the gene of about 300 nucleotides, preferably of about 200 nucleotides, particularly of about 100 nucleotides. A pausing region corresponds to such region in which the transcriptional activity is low, preferably less than 20%, particularly less than 10%, quite particularly less than 5% relative to the activity in a region of about 300 nucleotides directly downstream of the transcription initiation site, particularly when the run-on assay is performed for a prolonged time period, i.e. for a period of 5 to 10 minutes. Nuclei to be used in the run-on assay can be obtained by nuclei purification methods using either transiently or stably transformed cells carrying the gene respectively extra- or intrachromosomally. If transgenic plants are available in which the nuclear genome is transformed with the gene under control of appropriate plant gene regulatory sequences, the pausing region can be determined by nuclear run-on assays, supplemented by DMS footprinting analysis, as for instance described in the examples, and/or the KMNO pausing assay (Morrett and Buck, 1989; Sasse-Dwight and Gralla, 1988; Cannon et al, 1990).

Once the pausing region has been determined parts or all of it (generally regions of about 100 to 300 nt in length) can be cloned into two orientations in a suitable transcription initiation-probe vector (Cornelissen and Vandewiele, 1989a). Such a vector can, for example, be obtained by placing part or all of the pausing region downstream of an enhancer of a plant promoter and upstream of a DNA sequence that can be transcribed and the transcript of which can be uniquely detected in plant cells. A preferred example of such an enhancer is the enhancer or "B" region of the 35S promoter as described by Benfey et al (1990), but other known enhancer regions can also be used (as for instance the enhancer of the TR2' promoter). Preferred examples of a transcribable region in the transcription initiation probe-vector are the coding regions of the bacterial chloramphenicol acetyl transferase gene (cat) or the basta-resistance gene (Cornelissen and Vandewiele, 1989a), followed by a suitable 3' end formation and polyadenylation sequence. When these vectors are introduced into plant cells such as tobacco or maize protoplasts, one can then detect the accumulation of particular transcript species which are initiated from the presumed cryptic promoter by hybridization with a probe derived from the transcribable region of the transcription initiation probe-vector. Primer extension analysis or Si mapping of the transcripts then allows the determination of the transcription initiation site which in turn facilitates the detection of potential DNA regulatory elements, such as CCAAT and TATA boxes that are recognized by the plant cell. If known DNA regulatory elements in a suitable configuration to be recognized by the plant cell (e.g. a CCAAT box and a TATA box separated by about 20 to 50 nucleotides) are found in the sequence this is already a strong indication of the presence of a cryptic promoter and this can be confirmed by assaying for the ability to initiate transcription by placing the region containing these elements in the transcription initiation-probe vector as described above. Typically the start site of transcription is maintained when the enhancer is moved relative to the cryptic promoter over distances shorter than 50 nucleotides, preferably 100 nucleotides, more preferably 200 nucleotides.

In accordance with this invention, an abortive intron in the coding region of a particular gene, preferably a Bt ICP gene, can be detected by the following procedure:

The coding region of the gene is placed under control of suitable plant regulatory sequences in a suitable vector and introduced in plant cells, such as tobacco or maize protoplasts. About 5 to 7 hours after DNA delivery, total RNA is extracted. cDNA is prepared from the mRNA that is present in the plant cells according to conventional methods. Subsequently overlapping regions of the full size precursor mRNA expected to be produced from the introduced gene are amplified by means of PCR, using the previously synthesized cDNA as a substrate and using gene specific oligonucleotide primer pairs that lie between the transcript start site and the 3' end formation site.

In general overlapping regions of about 500 to 700 nucleotides are amplified, but this can be supplemented with amplification of increasingly larger overlapping regions e.g. amplification of overlapping regions of about 1000 nucleotides possibly followed by amplification of overlapping regions of about 2000 nucleotides will be generally suitable for this purpose.

The amplified products are then analyzed and any product that is smaller in size than that expected on the basis of full-size, mature mRNA is purified and sequenced. A comparison of the sequence of such shorter amplified products with the sequence of the expected full size precursor mRNA then allows the identification of gaps in the amplified products corresponding to introns. This in turn allows the identification of presumed intron splice sites at the 5' and 3' ends of the introns in the expected full-size mRNA. Inactivation of the 5' splice site and reintroduction of the gene into plant cells will allow to distinguish between abortive and partially active introns. If the intron is abortive, inactivation of the splice site will result in significant increases in full size mRNA levels, whereas inactivation of the partially active intron will result in a marginal increase of the full length mRNA level.

The routine system used for the identification of cryptic promoters or abortive introns as described above is the transient expression (TEX) protoplast system. For dicots, tobacco cells are preferred for the identification of the active process-directing sequence elements; for monocots, corn or rice cells provide the preferred test system. Of course, any plant cell, known in the art as suited for transient or stable transformation, can be used.

The identification and characterization of cryptic promoters and/or abortive introns of this invention allows the recognition of relatively small DNA sequence elements (the "target sequences") and their modification so as destroy the activity of these process- directing sequence elements in the plant cell.

It is preferred that such modifications be translationally neutral. "Translationally neutral modifications" as used herein are modifications that do not affect the amino acid sequence of the protein encoded by the gene. Preferred examples of such translationally neutral modifications are the changing, by means of nucleotide substitutions in the gene, of amino acid codons into others codons that encode the same amino acids. Such nucleotide substitutions can change A and T nucleotides into C and G nucleotides (PCT patent publication WO 91/16432), and for certain other translationally neutral modifications, C and G nucleotides may be changed to A and T nucleotides. Another preferred example of translationally neutral modifications is the introduction in the gene of at least one intron, known to be efficiently spliced in plant cells, so that the gene is transcribed into a precursor mRNA that is efficiently processed, by means of splicing of the introduced intron, into a mature mRNA that codes for the protein, preferably the Bt ICP. An intron known to be efficiently spliced in plant cells is any intron that is efficiently spliced out of a precursor mRNA in the plant cell. A suitable intron for use in plants, preferably in dicots, is the TA36 intron, as described in PCT patent publication WO 92/13957 or any other functional plant intron. Appropriate sites for insertion of the TA 36 intron or any other functional plant intron are determined according to well known general rules as outlined, for example, in Goodall and Filipowicz (1989) and Hanley and Schuler (1988).

Of course, translationally neutral nucleotide substitutions can be combined with the introduction of such introns in a foreign gene to be expressed in a plant.

The DNA regulatory elements, such as the CCAAT and/or TATA boxes, present in a cryptic promoter are preferred target sequences for modification. Thus the sequence of such DNA regulatory elements can be changed by transitionally neutral nucleotide substitutions of selected nucleotides and/or by insertion in that sequence of a suitable plant intron. However, plant cell recognition of the cryptic promoter can be reduced or eliminated by making substantial translationally neutral changes throughout the zone of 20 to 90, preferably 20 to 50, nucleotides upstream of the experimentally determined transcription initiation site. Preferably, such substantial changes will comprise making the maximum possible number of translationally neutral nucleotide substitutions within this zone. Also, the introduction of a suitable plant intron at any appropriate position in this zone is believed to reduce the activity of the cryptic promoter.

With respect to the abortive introns, it is believed that the abortive intron splice sites are of particular importance or the entry of the precursor mRNA containing the abortive intron in the abortive splicing pathway. Abortive introns are preferably inactivated by translationally neutral modifications in the coding region of the gene, preferably the Bt ICP gene, in the sequence corresponding to that surrounding at least the 5' (or upstream) abortive splice site in the precursor mRNA transcribed from the gene in a plant cell. Of course these modifications may be supplemented with, or even replaced by, modifications in the sequence of the coding region corresponding to that surrounding the 3' (or downstream) abortive splice site and/or the branch point (Brown, 1986). Preferred target sequences are thus believed to be a sequence of about 10 nucleotides, particularly a sequence of about 5 nucleotides, quite particularly a sequence of about 3 nucleotides, on either side of the sites that, in the precursor mRNA transcribed from the gene, correspond to the 5' and/or 3' abortive splice sites of the abortive intron, preferably its 5' GT and/or its 3' AG nucleotides. Abortive introns according to this invention have certain essential characteristics of plant introns as described for example by Goodall and Filipowicz (1989, 1990). Furthermore, examples of target sequences for abortive intron modification can be found in the consensus RNA sequences essential for intron splicing (Padgett et al, 1986; Aebi and Weismann, 1988) in plant cells as described by Hanley and Schuler (1988) as follows (' refers to the splice position): N A/U G' G U A A G U/A A/U U/A U/A at the 5' border of introns of dicots and U/A U/A U/N U/A U/A U/A U/AA/U U/A U/A U G/A C/U A G' at the 3' border of introns of dicots; and A/C/G A G' G U A A/U C U/C U/A U/C U/N at the 5' border of introns of monocots and U/C U/C U/G U/A U/C U/G U/N U/N U G/N C A G' at the 3' border of introns of monocots. Surprisingly, many non-plant genes, particularly Bt ICP genes, have been found to encode the following portions of the consensus RNA sequences of Hanley and Schuler (1988) that are essential for intron splicing in plant cells: GUAAG or GUAUG, particularly GUAAG, downstream (i.e., 3') of the upstream (i.e., 5') intron splice position; and AG upstream of the downstream intron splice position.

Thus the modification of a cryptic promoter and/or of the DNA encoding an abortive intron, preferably in specific target sequences, particularly by removing the essential characteristics or destroying the DNA encoding the consensus RNA sequences, as described above, results in an increased amount of full-size mRNA that can be translated to produce the protein encoded by the gene.

As used herein, "modified gene" should be understood as a DNA sequence, preferably one that encodes a Bt ICP, and in which, in at least one process-directing sequence element of the coding region, the nucleotide content of at least one codon has been changed by a translationally neutral modification that results in the inactivation of such a process-directing sequence element. Preferably, only minor modifications are made go the coding region of the Bt ICP gene. In particular, the modifications involve changing less than 10%, preferably less than 3%, particularly less than 1%, of the nucleotides in the coding region. In this regard, less than 10%, preferably less than 3%, particularly less than 1%, of the nucleotides in the coding region of the gene are changed from A or T nucleotides to G or C nucleotides. However, modifications of the coding region in accordance with this invention do not require the introduction of plant preferred codons, nor do they require that only A and T nucleotides are changed to G and C nucleotides. Preferably, each of the process-directing sequence elements is modified by changing only few nucleotides, so that the element is inactivated in the given plant cell, and so that the nucleotides encode the same amino acids. However, in some instances, some amino acids can be changed, such as when an encoded Bt ICP retains at least substantially the same insecticidal properties.

This invention is preferentially applied to genes which are to be expressed into certain plant species but that originate from organisms that are only distantly related to those plant species, e.g., expressing bacterial or animal genes in plants, monocot genes in dicots or dicot genes in monocots. In this regard the invention is particularly useful for modifying genes which are A+T-rich, particularly genes which contain more than 50% A+T in certain regions, such as Bt ICP genes, especially the cryI genes, more specifically the cryIAb gene.

The present invention will be exemplified by means of the cryIAb or bt2 gene of *Bacillus thuringiensis*. Thus it has been shown previously that the expression pathway of a Bt ICP gene, such as bt2, bt14, bt15 and bt18, is specifically inhibited at the nuclear level in plant cells (PCT patent publication WO 91/16432 which is incorporated herein as reference). Nuclear run-on analysis with N28-220 nuclei, originating from tobacco cells and containing the bt884 construct (Vaeck et al., 1987), indicated that transcription elongation of the nascent Bt ICP mRNA was impaired between or close to nucleotides 700 to 1000 downstream of the start of transcription. Filter binding assays using labeled Bt DNA fragments spanning this region and protein extract prepared from tobacco nuclei revealed that this DNA region undergoes specific interactions with proteins present in nuclei (PCT publication WO 91/16432).

In vivo transcription initiation assays (Cornelissen and Vandewiele, 1989a) in which the 474 bp EcoRV-Bst1107I bt884 fragment is positioned downstream of the CAMV 35S enhancer, have now revealed that this region functions as a minimal promoter in tobacco and as such can interact with nuclear transcription factors. These interactions are the prime candidates that cause or affect the impaired elongation of transcription by RNA polymerase II through this region. By modification of this region to abolish specific protein binding, Bt ICP expression levels will increase. This region has been found to contain CCAAT- and TATA-sequences, which are conserved motifs, found in promoters of diverse origin (The Molecular Biology of the Cell, 1989).

Deletion analysis suggested that the low transcript levels produced by Bt ICP genes were not controlled by a single factor (PCT publication WO 91/16432). A study of the polyadenylated bt884 transcripts in N28-220 by cDNA-PCR revealed the occurrence of minor quantities of shorter transcript species. Sequence analysis of the PCR products demonstrated the presence of three cryptic introns in the bt884 coding region. It can not be excluded that additional or other splicing events, including abortive splicing, take place when the bt884 is expressed in other plant species. In accordance with the deletion analysis, this finding demonstrates that a plurality of inhibitory zones are present in the bt884 coding region.

Nevertheless, individual modifications of the bt884 or cryIAb6 coding region can significantly reduce the interference and/or inhibition of the expression of the full length mRNA encoded by the genes in plant cells at the level of transcript elongation, nuclear processing, nuclear accumulation and nuclear export. The modification(s) may also affect cytoplasmic regulation and metabolism of such mRNAs and their translation.

In addition, substitution mutations were made at the 5' splice sites of each of the three cryptic introns. These mutations are translationally neutral, and as such abolish splicing of the respective introns. bt884 or cryIAb6 genes carrying these modifications direct significantly higher levels of full length mRNA and ICP in tobacco cells compared to the wild-type gene.

Instead of modifying the codon usage of one or more inhibitory zones in a Bt ICP gene, such as bt884 or cryIAb6, at least one process-directing sequence element in each such zone, preferably each of such sequence elements in each inhibitory zone, is inactivated, preferably split by providing at least one intron within it. The intron preferably provided in the inhibitory sequence is efficiently spliced in the plant cell, and is not intended to provide a so-called "intron-mediated elevation of gene expression" as has been reported for several genes that were transiently introduced in corn cells (Callis et al, 1987). Instead, the intron is intended to destroy the functioning of the inhibitory sequences by dividing the sequence in two. This modification leaves the coding region of the Bt ICP gene otherwise unaffected, while changing its regulatory features in regard to processes preceding the accumulation of mature mRNA in the nucleus and/or cytoplasm. However, to optimize the splicing efficiency of precursor mRNAs, it may be necessary to modify the nucleotides flanking the introduced intron, preferably with at most three nucleotides, spread over at most two translational codons, to create optimal 5' and 3' splice boundaries. According to Brown (1986), 38 out of 64 possible nucleotide triplets can each serve as a 5' exon boundary flanking an intron in an endogenous plant gene in a plant, and any nucleotide can be used at the 3' exon boundary flanking such an intron. Triplets not described by Brown (1986) can also function as such 5' exon boundaries in a plant.

By way of example the 5' splice site of intron 2 was interrupted in the cryIAb6 coding region by introducing the intron sequence of the tobacco gene TA36. This modified gene directs elevated levels of full length cryIAb6 mRNA in tobacco cells.

In the modified Bt ICP gene all process-directing sequence elements, active in the plant cell, can be removed or destroyed, or only some can be removed or destroyed, depending on the expression level desired.

Preferably, the modified gene, such as the modified Bt ICP gene, is inserted in a plant genome downstream of, and under the control of, a promoter which can direct the expression of the gene in the plant cells. Preferred promoters include, but are not limited to, the strong constitutive 35S promoter (Odell et al, 1985) or duplicated 35S promoter (Kay et al, 1987) of cauliflower mosaic virus; 35S promoters have been obtained from different isolates (Hull and Howell, 1987). Other preferred promoters include the TP1' promoter and the TR2' promoter (Velten et al, 1984). Alternatively, a promoter can be utilized which is not constitutive but rather is specific for one or more tissues or organs. For example, the modified gene can be selectively expressed in the green tissues of a plant by placing the gene under the control of a light-inducible promoter such as the promoter of the ribulose—1,5—biphosphate—carboxylase small subunit gene as described in EPA 86300291.1. Another alternative is to use a promoter whose expression is inducible by temperature or chemical factors.

It is preferred that the coding region of the modified gene, such as the modified Bt ICP gene, be inserted upstream of suitable 3' transcription regulation signals (i.e., transcript 3' end formation and polyadenylation signals) derived from the chalcone synthase gene (Sommer and Saedler, 1986) or Cauliflower Mosaic Virus (Mogen et al, 1990), the octopine synthase gene (Gielen et al, 1984), or T-DNA gene 7 (Velten and Schell, 1985).

In accordance with this invention, all or part of a modified gene of this invention, such as a modified Bt ICP gene, can be stably inserted in a conventional manner into the nuclear genome of a plant cell, and the so-transformed plant cell can be used to produce a transgenic plant showing improved expression of the modified gene. In this regard, a disarmed Ti-plasmid, containing the modified gene, in Agrobacterium (e.g., *A. tumefaciens*) can be used to transform a plant cell using the procedures described, for example, in EP 116,718 and EP 270,822, PCT publication 84/02913, EPA 87400544.0 and Gould et al (1991) (which are incorporated herein by reference). Preferred Ti-plasmid vectors contain the foreign DNA sequence between the border sequence, or at least located to the left of the right border sequence, of the T-DNA of the Ti-plasmid. Of course, other types of vectors can be used to transform the plant cell, using procedures such as direct gene transfer (as described, for example, in EP 233,247), pollen mediated transformation (as described, for example, in EP 270,356 PCT publication WO85/01856, and U.S. Pat. No. 4,684,611), plant RNA virus-mediated transformation (as described, for example, in EP 67,553 and U.S. Pat. No. 4,407,956), liposome-mediated transformation. (as described, for example, in U.S. Pat. No. 4,536,475) and other methods such as the methods for transforming monocots such as the major cereals including corn, rice, wheat, barley and rye, as described in PCT patent publication WO 92/09696. In case the plant to be transformed is corn, other recently developed methods can also be used such as, for example, the method described for certain lines of corn by Fromm et al (1990), Gordon-Kamm et al (1990), and Gould et al (1991). In case the plant to be transformed is rice, recently developed methods can also be used such as, for example, the method described for certain lines of rice by Shimamoto et al (1989), Datta et al (1990) and Hayashimoto et al (1990).

The resulting transformed plant of this invention shows improved expression of the modified gene, such as the modified Bt ICP gene, and hence is characterized by the production of high levels of protein, such as Bt ICP, encoded by the gene. Such a plant can be used in a conventional breeding scheme to produce more transformed plants with the same improved properties such as insect-resistance characteristics or to introduce the modified gene like the modified Bt ICP gene into other varieties of the same or related plant species. Seeds, which are obtained from the transformed plants, contain the modified gene as a stable genomic insert. It is believed that expression of a foreign gene in a plant can be improved in accordance with this invention for any plant such as corn, soybean, oilseed rape, wheat, lettuce, tomato and potato. However, the modification of genes intended to be expressed in monocots may require the translationally neutral modification of process-directing sequence elements having different DNA or RNA sequences from those active in dicots.

Furthermore, at least two modified Bt ICP genes, coding for two non-competitively binding Bt ICPs, can be cloned into a plant expression vector (EPA 89401499.2). Plants transformed with such a vector are characterized by the simultaneous expression of at least two modified Bt ICP genes. The resulting transgenic plant is particularly useful to prevent or delay development of resistance to Bg ICP of insects feeding on the plant.

This invention is thus based on the discovery that the coding region of foreign genes, particularly bacterial genes, quite particularly Bt ICP genes, may contain genetically cis-acting regulatory elements in their coding regions, particularly cryptic promoters and abortive introns, that seriously hamper the expression of these genes when they are introduced, under control of appropriate plant regulatory sequences such as plant promoters and 3' untranslated ends, in a plant cell environment. The discovery of such sequences allows the directed and limited modification of target sequences within the coding regions of such genes. In general less than about 10%, preferably less than about 3%, nucleotide modifications in the coding region are required in order to substantially alleviate the expression problem. Because only a relatively small number of modifications result in a substantial increase of foreign gene expression in plants, the modified genes produced on accordance with this invention are unlikely to contain newly introduced sequences that interfere themselves with expression of the gene in a plant cell environment.

The following Examples illustrate the invention and are not intended to limit its scope. The Figures and Sequence Listings, referred to in the Examples, are as follows:

BRIEF DESCRIPTION OF THE DRAWINGS

FIG. 1—Comparison of the transcriptional activity of neo and bt884 genes in nuclei of N28-220 of Example 1. The RNA extension reaction was performed in the presence of $^{13}$P UTP for 20 minutes at 30° C. Radioactively labeled RNA extracted from nuclei was hybridized with a molar excess of denatured neo and bt884 DNA which was immobilized on a nylon membrane. The positions and sizes of the DNA regions on the T-DNA are indicated. LB and RB refer to the left and right T-DNA borders, respectively. The 3' end formation and polyadenylation region of the g7 and ocs genes (Vaeck et al, 1987) are indicated. The relative abundance of hybridizing neo (left-hand column) and bt884 (right-hand column) mRNAs was measured both by scintillation counting and densitometric scanning of autoradiographs with different exposure times. Values were corrected for the UTP contents of the hybridizing RNA.

FIG. 2—Schematic representation of the DMs footprint of the bt884 coding region between nucleotides 668 and 834. Nucleotides hyper- and hypo-methylated in vivo relative to naked DNA by DMS are indicated by arrows pointing respectively downwards and upwards. See the scales at the right of the figure for quantification. All maintenance greater than 15% and hypersensitivities greater than 1.25 fold are shown. Boxed G-residues were not taken into account as the corresponding bands comigrated with dimers of the radioactively labeled primers. The CCAAT boxes are underlined.

FIG. 3A—Schematic view of the bt884 coding region with four PCR primer sets of Example 4. Nucleotide numbering is relative to the translation start codon. The orientations of the PCR primers are indicated by arrows, and the position of the 5' nucleotide of each primer is shown.

FIG. 3B—Schematic views of three DNA fragments (I, II and III) obtained by PCR reactions with primers PS58 and PS59. Numbering is relative to the translation start codon and refers to the 5' and 3' nucleotides of the introns in the bt884 coding region. The adjacent nucleotides located upstream and downstream of the 3' and 5' splice sites are shown.

Sequence Listing:
SEQ ID NO. 1: oligonucleotide PS48
SEQ ID NO. 2: oligonucleotide PS43
SEQ ID NO. 3: oligonucleotide PS38
SEQ ID NO. 4: oligonucleotide PS39
SEQ ID NO. 5: oligonucleotide PS47
SEQ ID NO. 6: oligonucleotide PS44
SEQ ID NO. 7: oligonucleotide PS38
SEQ ID NO. 8: oligonucleotide PS46
SEQ ID NO. 9: oligonucleotide PS45
SEQ ID NO. 10: oligonucleotide PS58
SEQ ID NO. 11: oligonucleotide PS59
SEQ ID NO. 12: oligonucleotide PS61
SEQ ID NO. 13: oligonucleotide PS62
SEQ ID NO. 14: oligonucleotide PS63
SEQ ID NO. 15: oligonucleotide PS64
SEQ ID NO. 16: oligonucleotide PS65
SEQ ID NO. 17: oligonucleotide PS66
SEQ ID NO. 18: oligonucleotide RVA-5a
SEQ ID NO. 19: oligonucleotide RVA-5b
SEQ ID NO. 20: oligonucleotide RVA-6a
SEQ ID NO. 21: oligonucleotide RVA-6b
SEQ ID NO. 22: plasmid pJD884
SEQ ID NO. 23: plasmid pPS0212

Unless otherwise stated in the Examples, all procedures for making and manipulating recombinant DNA are carried out by the standardized procedures described in Sambrook et al, *Molecular Cloning—A laboratory Manual*, Cold Spring Harbor Laboratory Press, N.Y. (1989).

Particular nucleotides in the bt884 and cryIAb6 genes, as used in the examples, are identified with respect to the sequence of the genes as given in SEQ ID NO. 22 and SEQ ID NO. 23 respectively.

Plasmid pJD884, the complete sequence of which is given in SEQ ID NO. 22, contains the bt884 gene and was used to construct plasmids pRVA0214 and pPS0212. In this regard pRVA0214 is identical to pJD884 except that the sequence containing the ATG translation initiation codon between nucleotide positions 7630 and 105 is replaced with the corresponding sequence between positions 7546 and 6 of SEQ ID NO. 23; this results in a deletion of 28 amino acids at the N-terminus of the bt884 gene, and the introduction of a Joshi translation initiation consensus sequence (The corresponding bt2-derived gene in pRVA0214 is designated as cryIAb22). Plasmid pPS0212, the complete sequence of which is given in SEQ ID NO. 23, differs from pRVA0214 by several translational neutral nucleotide substitutions in the regions located between nucleotides 1 to 30 and between 594 to 906.

EXAMPLE 1

Cryptic Promoter Activity

Nuclear run-on data obtained with transgenic tobacco N28-220, described in PCT patent publication WO 91/16432, indicated that the low nucleo-cytoplasmic full length bt884 mRNA flow is not due to interference of the bt coding region with transcription initiation at the TR2' promoter (FIG. 1) and that elongation by RNA polymerase II was inhibited between or close to nucleotides 700 and 1000 downstream of the transcriptional start site of the bt884 gene. Furthermore, DNA footprint analysis showed that in vivo DNA binding proteins interact with the bt884 DNA region between nucleotides 670 and 1202 (nucleotide positions are measured relatively to the translation initiation codon). The result of this interaction could be that RNA polymerase II complexes encounter difficulties in elongating transcripts in this region. Inspection of the region revealed the presence of a number of CCAAT boxes.

Figure 2:
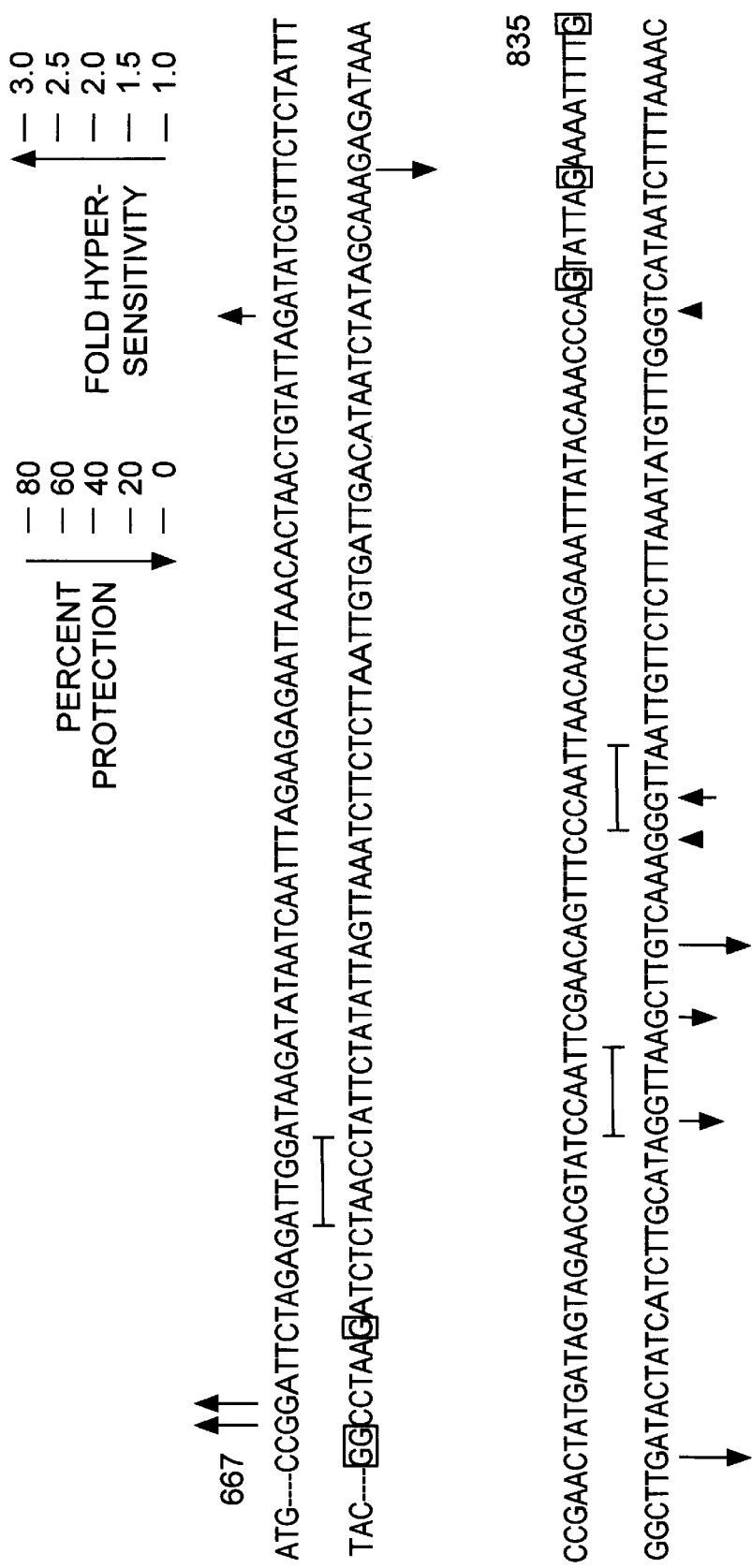

An in vitro dimethyl sulfate (DMS) footprint was carried out of the region 667 to 835, downstream of the translation start of bt884, to identify if in vivo the CCAAT boxes undergo a DNA-protein interaction. Protoplasts of N28-220 were treated for 3 minutes with 0.5% DMS, and total DNA was prepared (Dellaporta et al, 1983). A parallel reaction was carried out at pH 7.9 with 34 µg of deproteinized DNA of N28-220 in 200 µl TE (10 mM Tris, pH 7.9, 1 mM EDTA) to which 1 µl DMS was added. The incubation was stopped after three minutes by the addition of 100 µl 3M Tris, pH 8.0, followed by a phenol-chloroform extraction. The DNA samples were nicked 5' to the methylated G residues by a piperidine incubation (Maxam and Gilbert, 1980). DNA strands nicked near the bt2 (cryIAb) pausing region were amplified according to the ligation-mediated PCR method described by Mueller and Wold (1989) using 3.5 µg DNA samples for both reactions. The oligonucleotides used in the first priming reaction were: the oligonucleotide of SEQ ID NO. 1 for the coding strand and oligonucleotide of SEQ ID NO. 2 for the non-coding strand. The following linkers were ligated: the oligonucleotide of SEQ ID NO. 3 and the oligonucleotide of SEQ ID NO. 4. The ligation product was amplified by 19 PCR cycles, using for the coding and non-coding strands the respective oligonucleotides: the oligonucleotide of SEQ ID NO. 5 and the oligonucleotide of SEQ ID NO. 6, together with the lunker of SEQ ID NO. 7. A last amplification reaction of the coding and non-coding strands was done with respectively: the oligonucleotide of SEQ ID NO. 8 and the oligonucleotide of SEQ ID NO. 9 which were end-labeled with ⁻P. The reaction products were separated on a sequencing gel and visualized by autoradiography. The lanes were scanned three times with a LKB Ultrascan 2002 (Pharmacia LKB Biotechnology, Uppsala, Sweden) and compared by alignment of the recorded profiles. The nucleotide positions were plotted versus the ratio of the densitometric values of the G-residues at the different positions fin the in vivo and in vitro DMS footprints. A linear regression was determined by reiterated calculation using points that deviated less than 20% from the average slope. Hyper- and hypo-methylation levels were determined by calculating the relative deviation of the in vivo signals for the calculated relation. The result of the DMS footprint is shown in FIG. 2. The two closely spaced CCAAT boxes, and not a separately located C box more upstream, clearly show a modulated sensitivity to DMS in vivo relative to in vitro. This strongly suggests that these boxes undergo in vivo a protein-DNA interaction. As the bt coding region has a high AT content, the CCAAT boxes might be in the proximity of a functional TATA box and thus be part of a minimal promoter. To test this hypothesis, the 474 nucleotide EcoRV-Bst1107I bt884 fragment was positioned in a sense orientation between the CaMV 35S enhancer fragment and a promoterless cat gene to monitor possible transcription initiation events (Cornelissen and Vandewiele, 1989a). When introduced into tobacco protoplasts, the 35S enhancer CCAAT box fusion directs the synthesis of two discrete cat mRNA species. An S1-protection assay was carried out essentially as described by Sambrook et al (1989) to determine the 5' nucleotides of the cat mRNAs. This resulted in the identification of three different 5' termini. The 5' termini are present in approximately equimolar ratios and map at nucleotides 774, 775, 777; nucleotides 833, 834, 836; and nucleotide 841, relative to the translation start site of bt884. This finding shows that this region functions as a minimal promoter element and as such can interact with transcription factors. The consequence of this interaction is believed to result in the incapacity of RNk polymerase II to of transcribe efficiently this region.

EXAMPLE 2

Detection of bt884 mRNA Processing

PCT patent publication WO 91/16432 shows that the low cytoplasmic bt884 mRNA levels in tobacco are due to a limited flow rate of full length bt884 mRNA to the cytoplasm. The run-on analysis in combination with the deletion analysis described in PCT publication WO 91/16432 show that cryIAb transcript elongation in N28-220 is hindered between or close to nucleotides 700 and 1000, downstream of the start site of transcription initiation and that either several regions of the cryIAb coding region are involved in this process or transcriptional pausing at a cryptic promoter is not the sole process which interferes with expression.

To determine whether other processes are interfering with cytoplasmic bt884 mRNA accumulation, the integrity of the polyadenylated bt884 transcripts expressed by N28-220 was analyzed. The bt884 mRNA accumulates at levels which are below the detection limit of conventional Northern blot analyses of total RNA (Vaeck et al, 1987). The bt884 mRNA expressed by N28-220 was therefore studied as follows.

Mesophyll protoplasts of N28-220 were prepared as described by Denecke et al (1989). Total RNA was extracted according to Jones et al (1985), and a cDNA reaction was carried out using, as a DNA primer, oligo(dT) essentially as described by Kawasaki (1990). The first strand was used to amplify a specific DNA fragment employing the Polymerase Chain Reaction (PCR) as described by Kawasaki (1990) using the following sets of primers:
set A: PS66 and PS64,
set B: PS63 and PS65,
set C: PS58 and PS59,
set D: PS61 and PS62,
the primers being shown in the sequence listing as follows: PS58 in SEQ ID NO. 10, PS59 in SEQ ID NO. 11, PS61 in SEQ ID NO. 13, PS62 in SEQ ID NO. 13, PS63 in SEQ ID NO. 14, PS64 in SEQ ID NO. 15, PS65 in SEQ ID NO. 16, and PS66 in SEQ ID NO. 17.

Figure 3A:
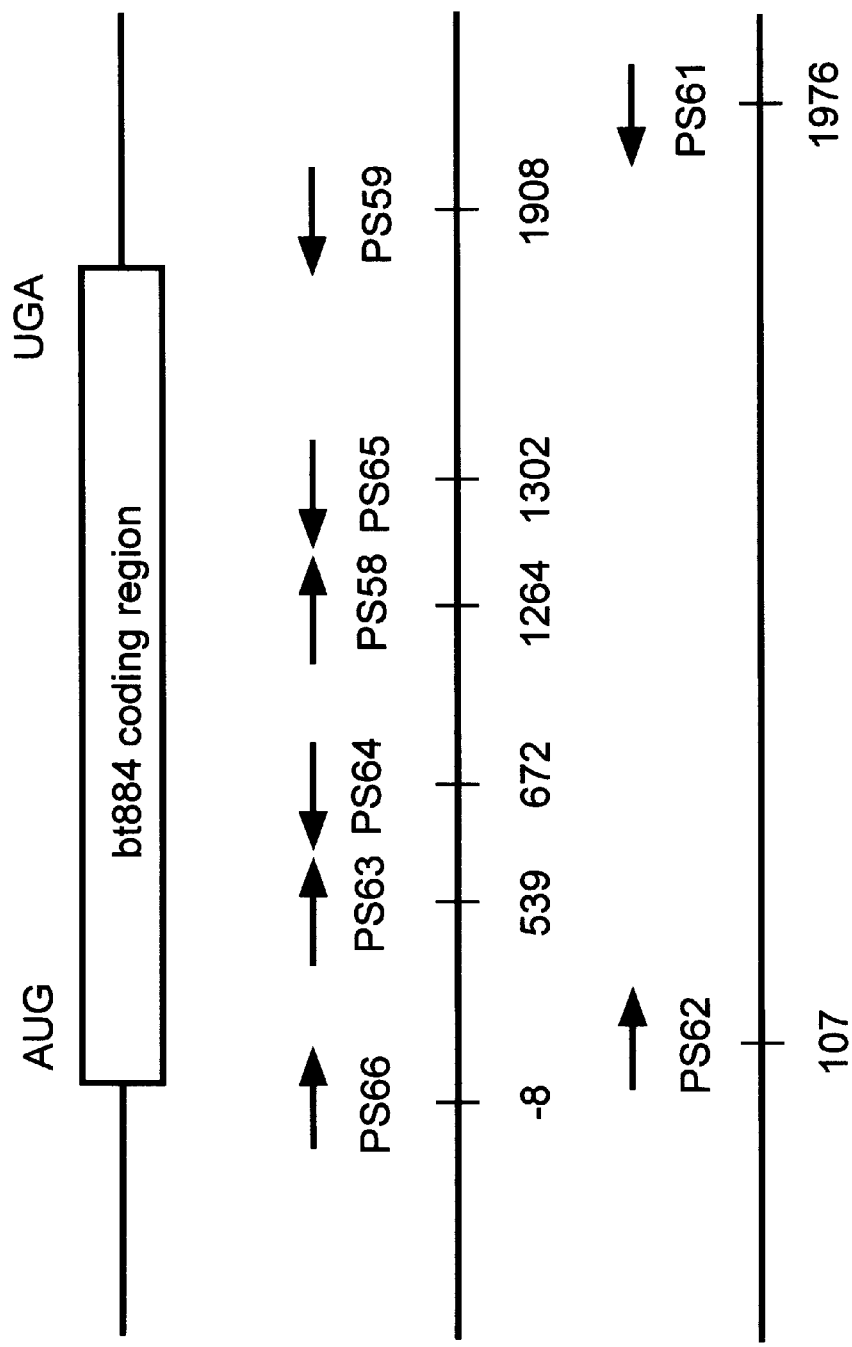

The amplified DNA products were run on a nondenaturing polyacrylamide gel, and primer sets k and B yielded DNA fragments of the expected size (FIG. 3a). Primer set C yielded, in addition to the expected DNA fragments, two additional DNA species of smaller size (II and III in FIG. 3b). Sequence analysis (Maxam and Gilbert, 1980) of the DNA fragments generated by primer set C revealed the presence of one and two deletions in the amplified bt884

Figure 3B:
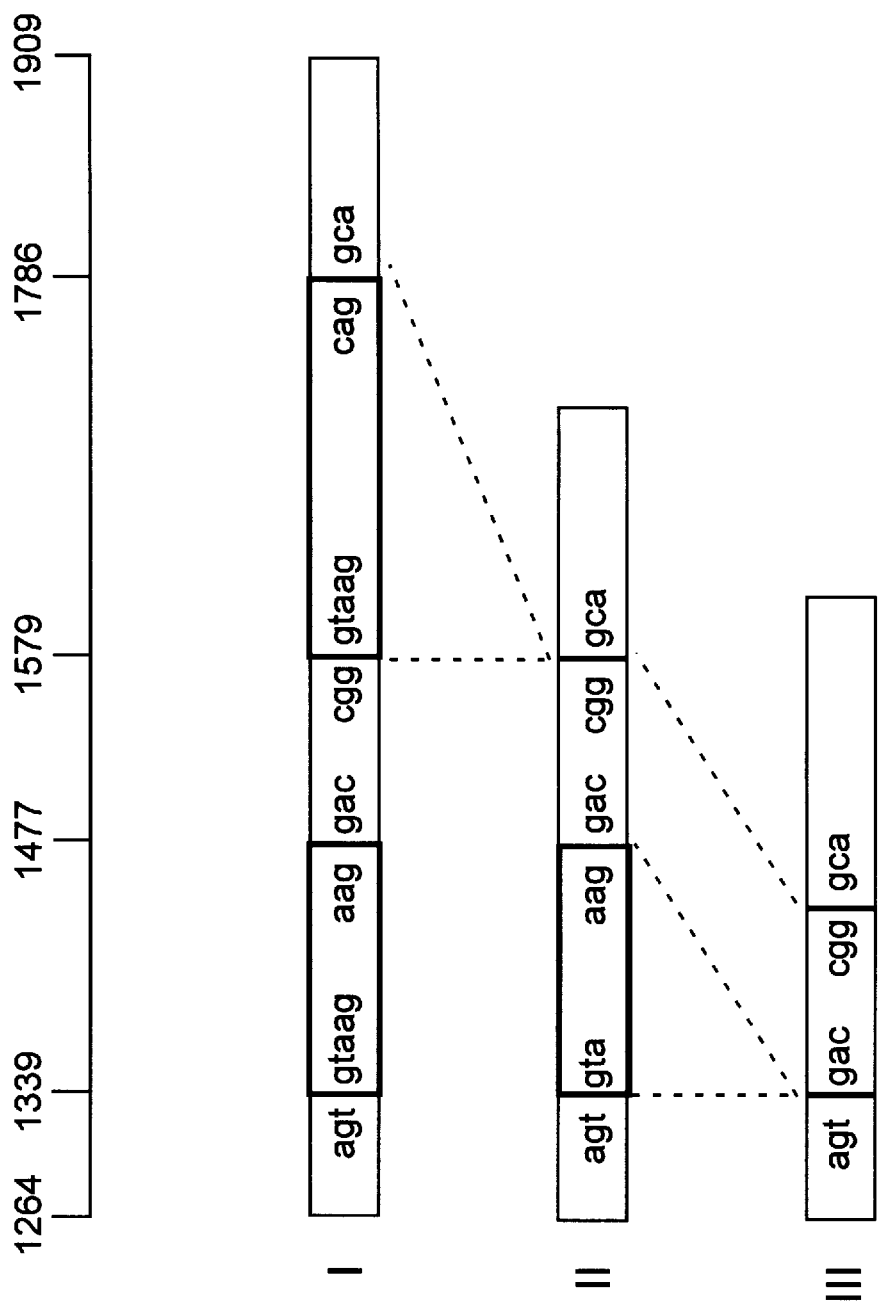

DNA sequences II and III, respectively. The nucleotide sequences of the extremities of the deleted portions are in agreement with the sequences of consensus sites of plant intron borders of Hanley and Schuler (1988) i.e., GT at the 5' end of each deleted portion and AG at the 3' end of each deleted portion (FIG. 3b). The size of the deletions was respectively 208 and 139 nucleotides. Primer ser D yielded in addition to the expected DNA product, four smaller PCR products. Sequence analysis of these fragments confirmed the occurrence of the 208 nucleotides deletion and the combination of the 208 and 139 nucleotides deletion as was seen with the cDNA-PCR analysis using primer set C, as well as the combination of the 208 nucleotides and a novel 929 nucleotides deletion. The extremities of this latter deleted sequence agree with the consensus sites of 5' and 3' RNA splice sites. The deletions thus reveal that the bt884 precursor mRNk undergoes splicing, the exact location of two of its cryptic introns is shown in FIG. 3b. The introns in FIG. 3b, at position 1339 to 1477 and position 1579 to 1786, relative to the translation start site, were named "intron 1" and "intron 2", respectively. The intron at position 549 to 1477 was named "intron 3".

EXAMPLE 3

Construction of Modified Bt ICP Genes

The bt2 coding region, which has been modified in PCT publication WO 91/16432, was either the bt884 or bt860-neo coding region (Höfte et al, 1986; Vaeck et al, 1987). One example of such a modified bt2 coding region is the cryIAb6 coding region, which is derived from the bt884 coding region (Höfte et al, 1986) and has been modified (with the purpose to restore the elongation efficiency) between its nucleotides 590 (XbaI site) and 917 (EcoR: site), affecting 63 of the 107 codons within this fragment.

In a similar way, the CCAAT boxes at nucleotides 772 and 789 of the bt884 coding sequence (in plasmid pJD884) are specifically removed to demonstrate that these process-directing sequence elements are involved in inhibition of transcript elongation. The oligonucleotides RVA-5 and RVA-6 are used: to modify the proximal CCAAT box by changing its A at position 774 into a G; and to modify the proximal CCAAT box by changing its A at position 792 into a G or by changing its A and T at positions 792 and 793 into a G and C, respectively. The resulting construct changed at positions 774 and 792 is called "pRVA0201", and the resulting construct changed at positions 774, 792 and 793 is called "pRVA0202". RVA-5 is a mixture of oligonucleotides of SEQ ID NO. 18 and SEQ ID NO. 19; and RVA-6 is a mixture of the oligonucleotides of SEQ ID NO. 20 and 21, that are complementary to RVA-5.

The PCR-mediated mutagenesis procedure described by Ho et al (1989) is used to incorporate the nucleotide sequences of the RVA-5 and RVA-6 fragments into a 1091 bp SpeI-EcoNI fragment of bt884 to change its CCAAT boxes at nucleotides 772 and 789. pRVA0201 and pRVA0202 are then introduced by electroporation into tobacco SR1 protoplasts for expression evaluation. Gene expression is found to be significantly improved.

The cryptic introns in the bt884 mRNA located at positions 1339–1477 (intron 1), 1579–1786 (intron 2) and 549–1477 (intron 3), relative to the translation start site, are functionally removed by the introduction of translationally neutral base substitutions at the appropriate positions in the bt884 coding region. The mutations are chosen such that the cryptic intron splice sites present on the bt884 coding region, which are necessary for the occurrence of splicing, become non-functional. Specifically, the 5' splice site of intron 1 was changed from AGT:GTAAGT into TCT:GTAACG, the 5' splice site of intron 2 was changed from CGG:GTAAGA into CGT:GTCCGG, and the 5' splice site of intron 3 was changed from AAG:GTGGGG into GCG:CTGGGG. The modifications were introduced each independently into plasmid pRVA0214 that carries the cryIAb22 gene. This gene is a derivative of bt884 that lacks the first 28 codons and has a GCU codon following the translation start signal. Furthermore, plasmid pRVA0214, which is derived from pJD884 (SEQ ID NO. 22), carries a chimeric cat reporter gene that serves as an experimental internal control in transient expression assays (Denecke et al, 1989). In a next step, the different 5' splice site modifications were combined resulting in a series of pRVA0214 derivatives carrying cryIAb genes with a modified 5' splice site of intron 1; intron 1 and 2; intron 1 and 3; intron 1, 2 and 3; intron 2; intron 2 and 3; and intron 3.

The plasmids were introduced into SR1 mesophyll protoplasts and 7 hours after delivery the expression of the different modified cry genes and of the cat gene was measured at the mRNA and protein level. An overview of the data is given in Table 1.

These data show that the genes modified at the 5' splice site of intron 2 give the highest ICP expression. When combined with modification in the 5' splice sites of intron 1 and 3, ICP expression further improves.

The relative ICP production rate was determined essentially as described by Denecke et al (1989, Table 2). This revealed that the splice site modifications greatly improve ICP production in time. In addition, a derivative of the cryIAb6 gene was made that carries the modified 5' splice sites of intron 2. Expression of this gene (cryIAb14) was compared with cryIAb6 at the mRNA and protein synthesis level. As shown in Table 2, the modification of the 5' splice site of intron 2, results in increased RNA level and greatly improves the ICP production level.

Taken together, these data demonstrate that the cryptic introns in bt884, particularly intron I and II, even more particularly intron II, cause abortive splicing of the bt884 precursor mRNA.

EXAMPLE 4

Cloning and Expression of Modified Bt ICP Genes in Tobacco and Potato Plants

Using the procedures described in U.S. patent application 821,582, filed Jan. 2, 1986, and EPA 86300291.1, EPA 88402115.5 and EPA 89400428.2, the modified Bt ICP (i.e., bt2) genes of Example 3 are inserted into the intermediate T-DNA vector, pGSH1160 (Deblaere et al, 1988), between the vector's T-DNA terminal border repeat sequences.

To obtain significant expression in plants, the modified Bt ICP genes of Example 3 are placed under the control of either the 35S promoter or the TR2' promoter (PTR2—Velten et al, 1984) and are fused to the transcript 3' end formation and polyadenylation signals of the chalcone synthase gene or the g7 gene.

In addition, the translation initiation context or site is changed in accordance with the Josh consensus sequence (Joshi, 1987) in order to optimize the translation initiation in plant cells. To this end, an oligo duplex is introduced to create the sequence, shown in SEQ ID NO. 23 from position 7561 to 6, at the translation initiation site. In this way, an additional codon (i.e., GCT) coding for alanine is introduced. Additionally, KpnI and BstXI sites are created upstream of the ATG translation initiation codon.

Using standard procedures (Deblaere et al, 1985), the intermediate plant expression vectors, containing the modified Bt ICP gene, are transferred into the Agrobacterium strain C58C1 Rif (U.S. patent application 821,582; EPA 86300291.1) carrying the disarmed Ti-plasmid pGV2260 (Vaeck et al, 1987). Selection for spectinomycin resistance yields cointegrated plasmids, consisting of pGV2260 and the respective intermediate plant expression vectors. Each of these recombinant Agrobacterium strains is then used to transform different tobacco plant cells (*Nicotiana tabacum*) and potato plant cells (*Solanum tuberosum*) so that the modified Bt ICP genes are contained in, and expressed by, different tobacco and potato plant cells.

The transgenic tobacco plants containing the modified Bt ICP genes are analyzed with an ELISA assay. These plants are characterized by a significant increase in levels of Bt (bt2) proteins, compared to a transgenic tobacco plant containing a non-modified Bt ICP (bt2) gene.

The insecticidal activity of the expression products of the modified Bt ICP (bt2) genes in leaves of transformed tobacco and potato plants is evaluated by recording the growth rate and mortality of larvae of tobacco hornworm (*Manduca sexta*), tobacco budworm (*Heliothic virescens*) and potato tubermoth (*Phthorimaea operculella*) fed on leaves of these two types of plants. These results are compared with the growth rate of larvae fed leaves from tobacco and potato plants transformed with the unmodified or parental Bt ICP (bt2) gene and leaves from untransformed potato and tobacco plants. Toxicity assays are performed as described in EPA 88402115.5 and EPA 86300291.1.

The insecticidal activity of transgenic tobacco plants containing the modified Bt ICP genes is determined against second and third instar larvae of *Heliothis virescens*. The control plants were not transformed. A significantly higher mortality rate is obtained among larvae fed on leaves or transformed plants containing and expressing the modified Bt ICP genes. Tobacco and potato plants containing the modified Bt ICP genes show considerably higher expression levels of Bt ICPs compared to tobacco and potato plants containing the unmodified Bt ICP gene.

Needless to say, this invention is not limited to tobacco and potato plants transformed with the modified Bt ICP gene. It includes any plant, such as tomato, alfalfa, sunflowers, corn, cotton., soybean, sugar beets, rapeseed, brassicas and other vegetables, transformed with the modified Bt ICP gene.

Nor is the invention limited to the use of *Agrobacterium tumefaciens* Ti-plasmids for transforming plant cells with a modified Bt ICP gene. Other known techniques for plant transformation, such as by means of liposomes, by electroporation or by vector systems based on plant viruses or pollen, can be used for transforming monocotyledonous and dicotyledonous plants wish such a modified Bt ICP gene. In this regard, monocots, including economically important crops such as cereals, particularly corn and rice, can be efficiently transformed using the procedures described in WO 92/09696, in which compact embryogenic callus or intact tissue, from which such callus can be obtained, is wounded by cutting and/or enzymatic degradation and then is transformed, for example by means of electroporation of linear DNA molecules.

Nor is the invention limited to the bt2 gene but rather encompasses all CryI, CryII, CryIII and CryIV Bt ICP genes. Indeed, sequences which can be present in cryptic promoters, e.g. CCAAT sequences, are found on both DNA strands (i.e., coding and non-coding strands) in all Bt ICP genes. By way of example, the positions of different perfect CCAAT sequences are listed in Table 3 below for the cryIB (bt14) gene, cryIC (bt15) gene, cryIE (bt18) gene and cryIIID (bt109P) gene. If such CCAAT sequences are in the correct environment, they can function as a cryptic promoter and thus interfere with transcription.

Similarly, plant intron splice sites are found within the coding region of many Bt ICPs. By using the properties of this invention abortive introns can be identified in these genes.

TABLE 1

| GENE | MOD. 5' SPLICE SITE | PLASMID NAME | REL. ICP LEVEL 7 HRS AFTER DELIVERY |
|---|---|---|---|
| bt884 | — | pJD884 | 1 |
| crvIAb22 | — | pRVA0214 | 3 |
| crvIAb28 | I | pRVA0219 | 4.3 |
| crvIAb24 | II | pRVA0218 | 8.4 |
| crvIAb21 | III | pRVA0213 | 3.2 |
| crvIAb26 | I, II | pRVA0220 | 9.2 |
| crvIAb27 | I, III | pRVA0216 | 4.2 |
| crvIAb23 | II, III | pRVA0217 | 8.5 |
| crvIAb25 | I, II, III | pRVA0215 | 9.4 |

Relative protein levels were determined by ELISA and CAT activity assays. Protein values are not absolute but rather show a general trend. The genes cryIAb28, -24, -21, -26, -27, -23, and -25 are derived from the cryIAb22 gene.

TABLE 2

| GENE | MOD. 5' SPLICE SITE | PLASMID NAME | ΔICP/hr | REL. ICP mRNA level |
|---|---|---|---|---|
| bt884 | — | pJD884 | 1 ± 0.25 | ND |
| crvIAb22 | — | pRVA0214 | 7 ± 2 | ND |
| crvIAb24 | II | pRVA0218 | 12 ± 4 | ND |
| crvIAb23 | II, III | pRVA0217 | 17 ± 5 | ND |
| crvIAb26 | I, II | pRVA0220 | 24 ± 3 | ND |
| crvIAb6 | — | pPS0212 | 17 ± 3 | 1.3 ± 0.3 |
| crvIAb14 | II | pRVA0208 | 37 ± 2 | 3.9 ± 0.6 | relative bt mRNA levels in total RNA of transiently transformed tobacco leaf protoplasts was determined 7 hrs after plasmid delivery corrected for cat mRNA levels essentially as described by Cornelissen and Vandewiele (1989b). ΔICP/hr is the relative ICP accumulation rate per hour corrected for the CAT accumulation rate per hour (ND: not determined).

ICP/CAT values were determined as described in patent publication no WO 91/16432. Time point samples were taken 0, 3.5, 7, 11 and 20 hrs after plasmid delivery. RNA and protein values are not absolute but rather show a general trend.

the genes cryIAb24, 23, and 26 are derived from cryIAb22, gene cryIAb14 is derived from cryIAb6.

TABLE 3

| DNA Strands | bt14 | bt15 | bt18 | bt109P |
|---|---|---|---|---|
| 5' -> 3' | 453-457 | 491-495 | 148-152 | 937-941 |
| | 823-827 | 763-767 | 763-767 | 1405-1409 |
| | 1072-1076 | 1539-1541 | 1234-1238 | 1870-1874 |
| | 1112-1116 | 1916-1920 | 1531-1535 | 1962-1966 |
| | 1507-1511 | | 1685-1689 | |
| 3' -> 5' | 192-196 | 671-675 | 943-947 | 456-461 |
| | 404-408 | 935-939 | 1492-1496 | 668-672 |
| | 871-875 | 962-966 | 1648-1496 | 1091-1095 |
| | 905-909 | 1759-1763 | | 1918-1922 |
| | 1042-1046 | | | |
| | 1480-1484 | | | |

The positions of other inhibitory sequences that can interact with CCAAT binding proteins are not listed in Table 3.

REFERENCES

Adang et al, Gene 36, 289–300 (1985).
Aebi and Weismann, Trends Genet. 3, 102–107 (1988).
Benfey et al, EMBO J. 9, 1677–1684 (1990).
Barton et al, Plant Physicl. 85, 1103–1109 (1987).
Brown, Nucleic Acids Research 14, 9549–9559 (1986).
Callis et al, Genes Dev. 1, 1183–1200 (1987).
Cannon et al, Nucl. Acids Res. 18, 1693–1761 (1990).
Connely and Manley, Cell 57, 567–571 (1989a).
Connely and Manley, Mol. Cell. Biology, 9, 5254–5259 (1989b)
Cornelissen and Vandewiele, Nucl. Acids Res., 17, 19–29 (1989a).
Cornelissen and Vandewiele, Nucl. Acids Res., 17, 833–843 (1989b).
Darnell, Nature 29,, 365–371 (1982).
Datta et al, Bio/Technology 8, 736 (1990).
Deblaere et al, Meth. Enzymol. 153, 277–292 (1988).
Deblaere et al, Nucl. Acids Res. 13, 4777–4787 (1985).
Delannay et al, Bio/Technology 7, 1265–1269 (1989).
Deliaporta et al, Plant Mol. Biol. Rep. 1, 19–21 (1983).
Denecke et al, Meth. Mol. Cel. Biol. 1, 19–27 (1989).
Dulmage, "Production of Bacteria for Biological Carroll of Insects" in "Biological Control in Crop Production" Ed. Paparizas D. C., Osmum Publishers, Totowa, N.Y., USA, pp. 129–141 (1981).
Fischhoff et al, Bio/Technology 5, 807–812 (1987).
Fromm et al, Bio/Technology 8, 833 et seq. (1990).
Gasser and Fraley, Science 244, 1293–1299 (1989).
Gielen et al, EMBO J 3, 835–845 (1984).
Gleave et al, J. Gen. Microbiol. 138, 55–62 (1992).
Goldberg and Margalit, Mosq. News 37, 355–358 (1977).
Goodall and Filipowicz, Cell 58, 473–483 (1989).
Goodall and Filipowicz, Plant Mol. Biol. 14, 727–733 (1990).
Gordon-Kamm et al, The Plant Cell 2, 603 et seq. (1990).
Gould et al, Plant Physiol. 95, 426–434 (1991).
Ha and An, Nucl. Acids Res. 17, 215–223 (1989).
Hanley and Schuler, Nucleic Acids Research 16, 7159–7176 (1988).
Hayashimoto et al, Plant Physiol. 93, 857 (1990).
Ho et al, Gene 77:51–59 (1989).
Höfte et al, Eur. J. Biochem 161, 273–280 (1986).
Höfte and Whiteley, Microbiol. Reviews 53, 242–255 (1989).
Hull and Howell, Virology 86, 482–493 (1987).
Jones et al, EMBO J. 4, 2411–2418 (1985).
Joshi, Nucl. Acids Res. 15, 6643–6653 (1987).
Katagiri and Chua, Trends Genet. 8, 22–27 (1992).
Kawasaki, in: PCR Protocols: a guide to methods and applications, edited by M. Innis, D. Gelfand, J. Sninsky and T., White, Academic Press Inc., pp. 21–27 (1990).
Kay et al, Science 236, 1299–1302 (1987).
Krieg et al, Z. Ang. Ent. 96, 500–508 (1983).
Maxam and Gilbert, Methods in Enzymology 65, 499–560 (1980).
McPherson et al, Bio/Technology 6, 61–66 (1988).
Mogen et al, The Plant Cell 2, 1261–1272 (1990).
Morett and Buck, J. Mol. Biol. 210, 65–77 (1989).
Meeusen and Warren, Ann. Rev. Entomol. 34, 373–381 (1989).
"The Molecular Biology of the Cell, Second Edition", Eds. Alberts et al, Garland Publishing Co., N.Y. and London (1989).
Mueller and Wold, Science 246, 780–786 (1989).
Odell et al, Nature 313, 810–812 (1985).
Padgett et al, Annu. Rev. Biochem. 55, 1119–1150 (1986).
Paul et al, Proc. Natl. Acad. Sci USA 84, 799–803 (1987).
Sambrook et al, Molecular Cloning—A laboratory Manual, Cold Spring Harbor Laboratory Press, N.Y. (1989).
Sasse-Dwight and Gralla, Proc. Natl. Acad. Sci USA 85, 8934–8938 (1988).
Schnepf et al, J. Biol. Chem. 260, 6264–6272 (1985).
Shimamoto et al, Nature 338, 274 (1989).
Sommer and Saedler, Mol. Gen. Genet. 202, 429–434 (1986).
Vaeck et al, Nature 327, 33–37 (1987).
Velten and Schell, Nucleic Acids Research 13, 6981–6998 (1985).
Velten et al, EMBO J 3, 2723–2730 (1984).
Widner and Whiteley, J. Bacterial 171, 965–974 (1989).

We claim:

1. A process for modifying the coding region of a *Bacillus thuringiensis* insecticidal crystal protein (Bt ICP) gene to be expressed in a plant cell; which process comprises the following steps:

identifying in the coding region of said Bt ICP gene at least one DNA sequence encoding an abortive intron; and modifying said coding region in a translationally neutral manner to obtain a modified coding region in which said at least one DNA sequence encoding an abortive intron has been inactivated, wherein said DNA sequence encoding an abortive intron can be identified by a process comprising the steps of:

(i) introducing said coding region under control of a plant-expressible promoter in plant cells, (ii) amplifying DNA fragments obtained from mRNA transcribed from said coding region in said plant cells, (iii) localizing a gap in said DNA fragments with a size smaller than the size expected for a mature mRNA by aligning said DNA fragments with the DNA sequence encoding a full-size unprocessed RNA;

wherein said gap is identified as a DNA sequence encoding an abortive intron when inactivation of splice sites surrounding the abortive intron results in an increase of the level of proper sized mRNA upon transcription in plant cells.

2. The process of claim 1, wherein the coding region of said Bt ICP gene is modified in a translationally neutral manner by introducing at least one of the following modifications in said coding region;
   a) introducing a DNA encoding an intron, spliced in the plant cell; and
   b) replacing amino acid codons in the coding region by other codons encoding the same amino acids.

3. The process of claim 2, wherein said coding region encodes a toxic portion of said ICP.

4. The process of claim 2, wherein the ATG translation initiation codon of said coding region has been replaced by the following sequence: AAAACCATGGCT.

5. The process of claim 4, wherein the coding region which is modified is that of the cryItb14 gene.

6. The process of claim 2, wherein said coding region encodes a Bt2 ICP and wherein the first 28 N-terminal codons of said coding region have been replaced by an ATG codon.

7. The process of claim 2, wherein said Bt ICP gene is a bt2 gene, a bt884 gene, a cryIAb6 gene, a cryIAb22 gene, a bt14 gene, a bt15 gene, or a bt18 gene.

8. The process of claim 7, wherein said Bt ICP gene is a bt2, a bt884 or a cryIAb22 gene and wherein a cryptic promoter is inactivated by translationally neutral modifications between nucleotide positions 742 and 813 in the coding region of bt884.

9. The process of claim 7, wherein said Bt ICP gene is a bt2, bt884, cryIAb22, or cryIAb6 gene and wherein said at least one DNA sequence encoding an abortive intron is inactivated by translationally neutral modifications in a region within 10 nucleotides of one or more of the following sequences in the coding region: AAG:GTGGGG, AGT:GTAAGT, and CGG:GTAAGA.

10. The process of claim 1, wherein said coding region after modification differs from a native coding region of a Bt ICP gene by having less than 3% of the nucleotides in said native coding region changed from A or T to G or C nucleotides.

11. The process of claim 1, wherein said coding region after modification differs from a native coding region of a Bt ICP gene by having less than 1% of the nucleotides in said native coding region changed from A or T to G or C nucleotides.

12. The process of claim 1, wherein the abortive intron is inactivated by translationally neutral modification in said coding region in about 3 to about 10 nucleotides on either side of the 5' and 3' abortive intron splice sites.

13. The process of claim 1, which further comprises the steps of:
   identifying in the coding region of said Bt ICP gene, at least one cryptic promoter in either a sense or an anti-sense orientation; and
   modifying said coding region in a translationally neutral manner to obtain a modified coding region in which said at least one cryptic promoter has been inactivated, wherein said cryptic promoter can be identified by a process comprising the steps of:
      (i) identifying a pausing region in said coding sequence inhibiting elongation of transcription by RNA polymerase II by means of run-on analysis on plant cell nuclei containing said coding sequence in their nuclear genome;
      (ii) cloning said pausing region or a part thereof in two orientations in a transcription initiation-probe vector downstream of an enhancer of a plant promoter and upstream of a DNA sequence that can be transcribed;
      (iii) introducing said vector into plant cells;
      (iv) detecting the accumulation of RNA species which is initiated from the pausing region; and
      (v) localizing the transcription initiation site in said RNA species;
   wherein said pausing region is identified as a cryptic promoter when said RNA is produced from a transcription initiation site located in said pausing region or the part thereof.

14. The process of claim 13, wherein said cryptic promoter comprises a CCAAT sequence or a TATA sequence.

15. The process of claim 13, wherein the abortive intron is inactivated by translationally neutral modification in said coding region in about 3 to about 10 nucleotides on either side of the 5' and 3' abortive intron splice sites, and wherein the cryptic promoter is inactivated by translationally neutral modification in said coding region of 20 to 90 nucleotides upstream of the experimentally determined transcription initiation site of said cryptic promoter.

16. A method of improving the production level of a Bt ICP protein in a plant cell, wherein said method comprises:
   identifying, in a coding region of a nucleic acid encoding said Bt ICP protein, at least one DNA sequence encoding a plant abortive intron;
   modifying said coding region in a translationally neutral manner to obtain a modified coding region in which said at least one DNA sequence encoding a plant abortive intron is inactivated; and
   introducing said modified coding region into said plant cell under the control of a promoter functional in a plant cell.

17. A process for protecting a plant from an insect pest, comprising the steps of:
   transforming the genome of the plant with a chimeric gene which comprises the following operably-linked DNA fragments:
      (1) a promoter for directing transcription in plant cells;
      (2) a modified coding region obtained by the process of claim 1;
      (3) a transcript 3' end formation and polyadenylation region functional in plant cells.

18. The process of claim 17, wherein said promoter is a 35S promoter, a TR1' promoter, or a TR2' promoter.

19. The process of claim 17, wherein said transcript 3' end formation and polyadenylation region is from the chalcone synthase gene.

20. A modified Bt ICP region, obtained from a native Bt ICP coding region by the process of claim 1 wherein said coding region of said Bt ICP gene is modified by making translationally neutral replacements in the DNA sequence encoding a splice site of said abortive intron.

21. A modified Bt ICP coding region of claim 20, wherein said modified Bt ICP coding region encodes a protein which is truncated at its N-and/or C-terminal end.

22. A modified Bt ICP coding region obtained from a native Bt ICP coding region by the process of claim 13 wherein the coding region of said Bt ICP gene is modified by making translationally neutral nucleotide replacements in said cryptic promoter and making translationally neutral nucleotide replacements in the DNA sequence encoding a splice site of said abortive intron.

23. A modified Bt ICP coding region obtained from a native Bt ICP coding region by the process of claim 1, wherein said at least one DNA sequence encoding an abortive intron is inactivated by making translationally neutral nucleotide replacements in said native Bt ICP coding region in about 3 to about 10 nucleotides on either side of a 5' and a 3' abortive intron splice site.

24. A modified Bt ICP coding region obtained from a native Bt ICP coding region by the process of claim 13, wherein said at least one cryptic promoter is inactivated by making translationally neutral modifications in said native Bt ICP coding region of 20 to 90 nucleotides upstream of the experimentally determined transcription initiation site of said cryptic promoter and said abortive intron is inactivated by making translationally neutral nucleotide replacements in a DNA sequence encoding a splice site of said abortive intron.

25. A modified Bt ICP coding region, obtained from a native Bt ICP coding region by making translationally neutral nucleotide replacements in the abortive intron 5' splice site motifs AGT:GTAAGT, CGG:GTAAGA and AAG:GTGGGG.

26. A plant cell, transformed to comprise the modified Bt ICP coding region of claim 20.

27. A plant, modified to comprise the modified Bt ICP coding region of claim 20.

* * * * *